United States Patent
Dutta

(10) Patent No.: US 11,058,328 B2
(45) Date of Patent: Jul. 13, 2021

(54) SYSTEM FOR SCREENING AND DIAGNOSIS OF DIABETES

(71) Applicant: Achyut Kumar Dutta, Sunnyvale, CA (US)

(72) Inventor: Achyut Kumar Dutta, Sunnyvale, CA (US)

(73) Assignee: Banpil Photonics, Inc., Santa Clara, CA (US)

( * ) Notice: Subject to any disclaimer, the term of this patent is extended or adjusted under 35 U.S.C. 154(b) by 397 days.

(21) Appl. No.: 14/985,391

(22) Filed: Dec. 31, 2015

(65) Prior Publication Data

US 2017/0188914 A1 Jul. 6, 2017

(51) Int. Cl.
*A61B 5/145* (2006.01)
*A61B 5/00* (2006.01)
*A61B 5/1455* (2006.01)

(52) U.S. Cl.
CPC ........ *A61B 5/14532* (2013.01); *A61B 5/1455* (2013.01); *A61B 5/14542* (2013.01); *A61B 5/14546* (2013.01); *A61B 5/681* (2013.01)

(58) Field of Classification Search
None
See application file for complete search history.

(56) References Cited

U.S. PATENT DOCUMENTS

| | | | | |
|---|---|---|---|---|
| 4,927,516 A | * | 5/1990 | Yamaguchi | C12Q 1/004 204/403.1 |
| 5,140,985 A | * | 8/1992 | Schroeder | A61B 5/14521 600/323 |
| 2011/0021894 A1 | * | 1/2011 | Mohanty | A61B 5/14532 600/345 |
| 2011/0256619 A1 | * | 10/2011 | Vacanti | C12N 5/0062 435/297.2 |
| 2013/0219995 A1 | * | 8/2013 | Dutta | G01N 27/04 73/31.06 |

FOREIGN PATENT DOCUMENTS

WO  WO 2010045247 A1 * 4/2010 ......... A61B 5/14521

* cited by examiner

*Primary Examiner* — Kaylee R Wilson
*Assistant Examiner* — Jay B Shah

(57) ABSTRACT

This invention relates to the means for detection of molecular and chemical matter utilizing multiple techniques covering electronics, optics, and imaging techniques. More particularly, this invention is related to detecting levels of certain molecules inside the body through non-invasive contact or non-contact with the body. More specifically, this invention is related to the means to detect levels of molecules associated with metabolic diseases, more particularly the early diagnosis of the disease, especially diabetes. This invention also relates to a medical device that utilizes electromagnetic waves of varying wavelengths and detects waves returned to the device.

11 Claims, 47 Drawing Sheets

Circuit

Circuit (top)

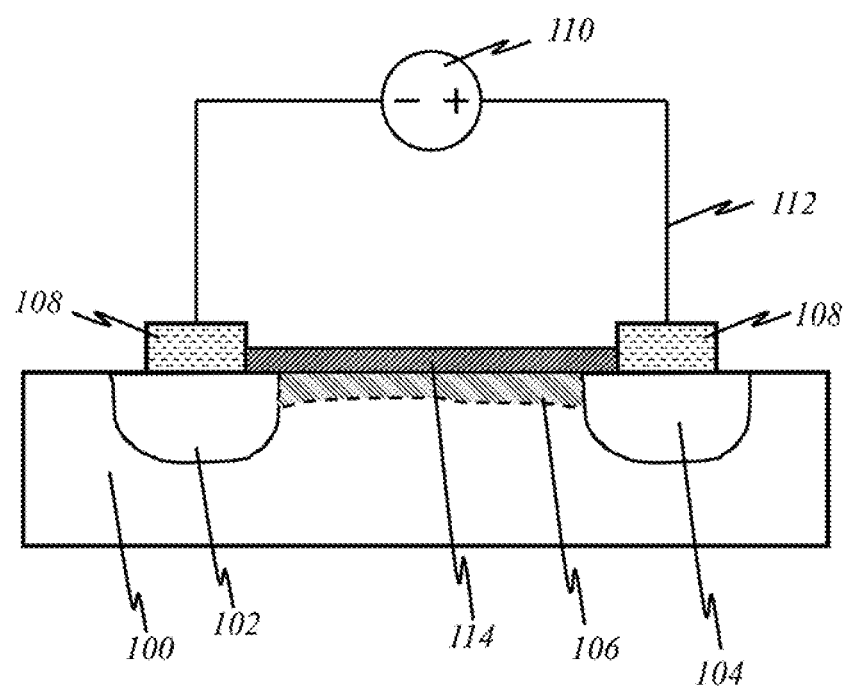
FIG. 1A Circuit

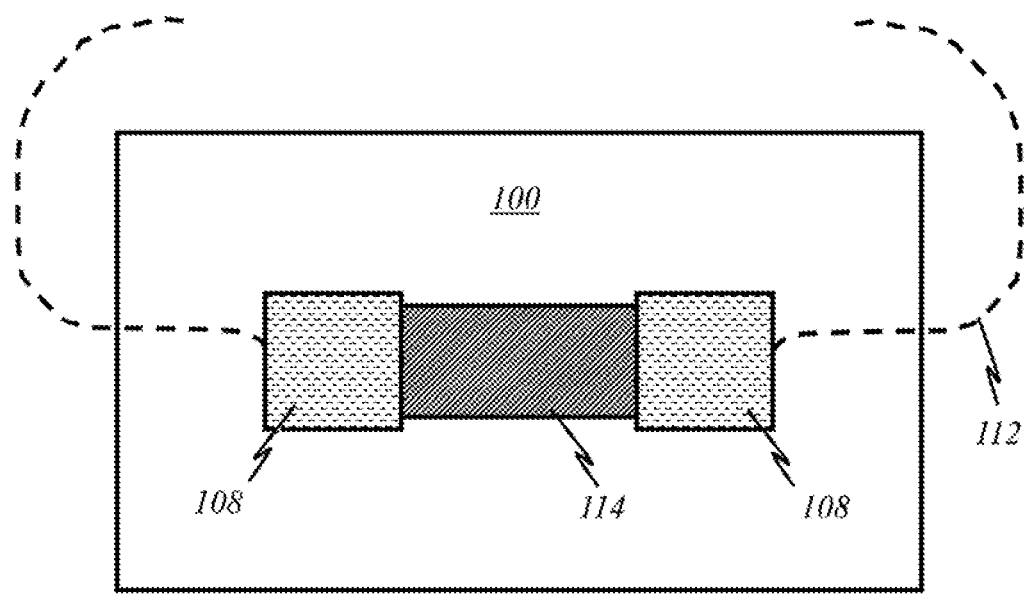
FIG. 1B Circuit (top)

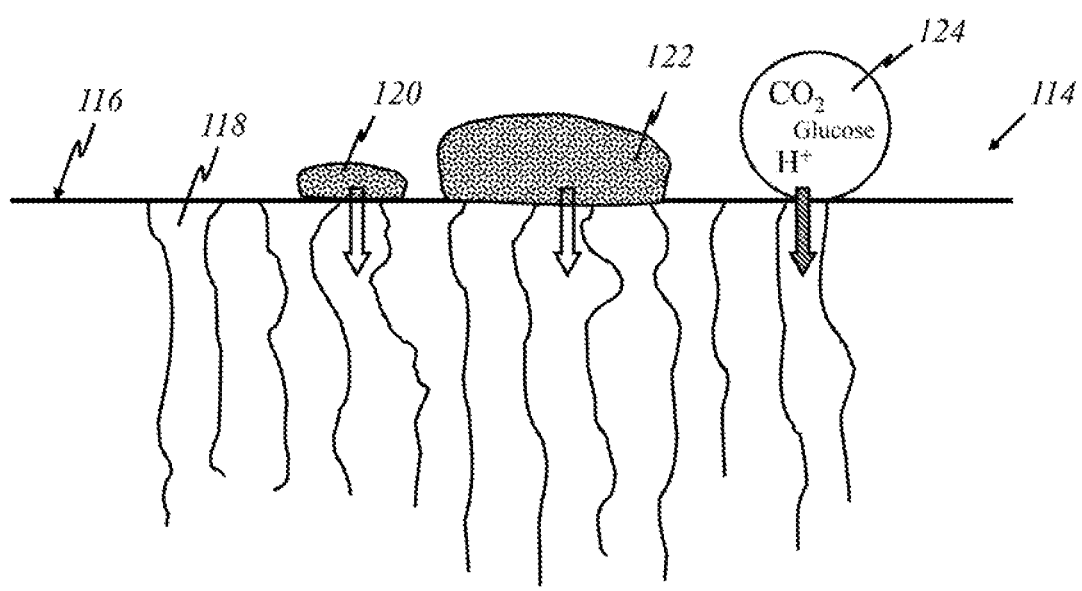
FIG. 1C nanomembrane

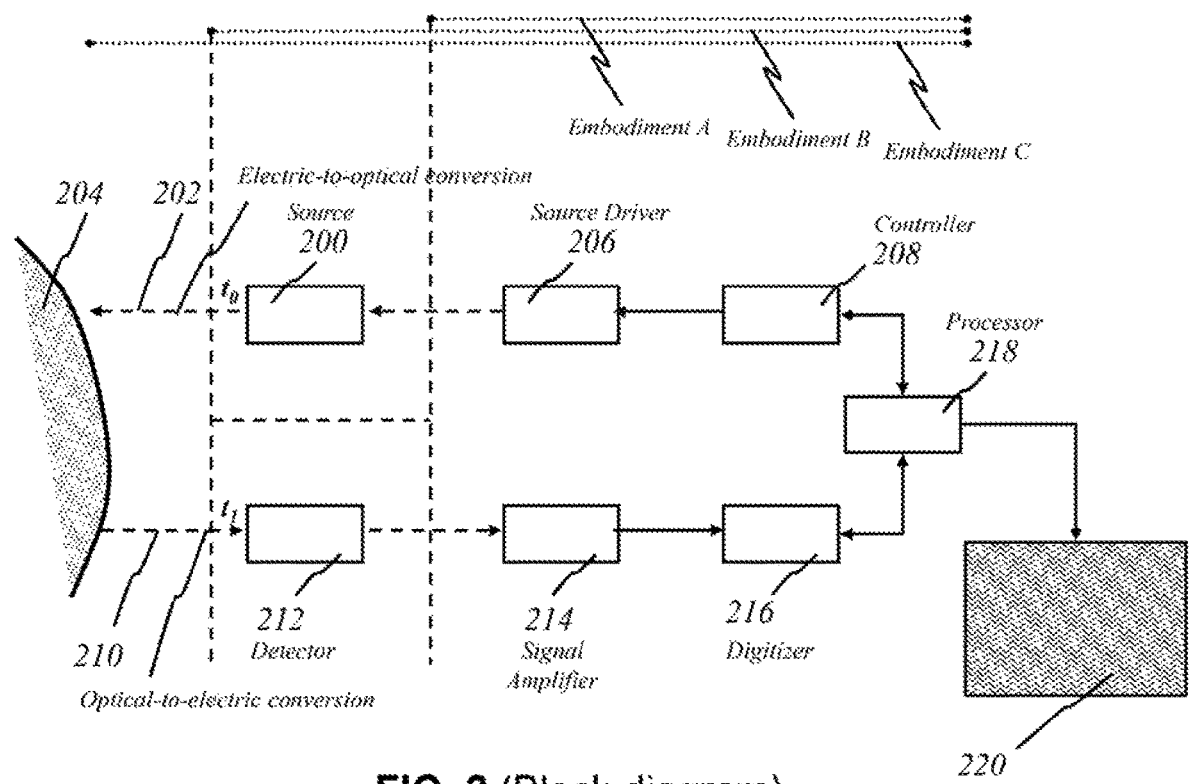
FIG. 2 (Block diagram)

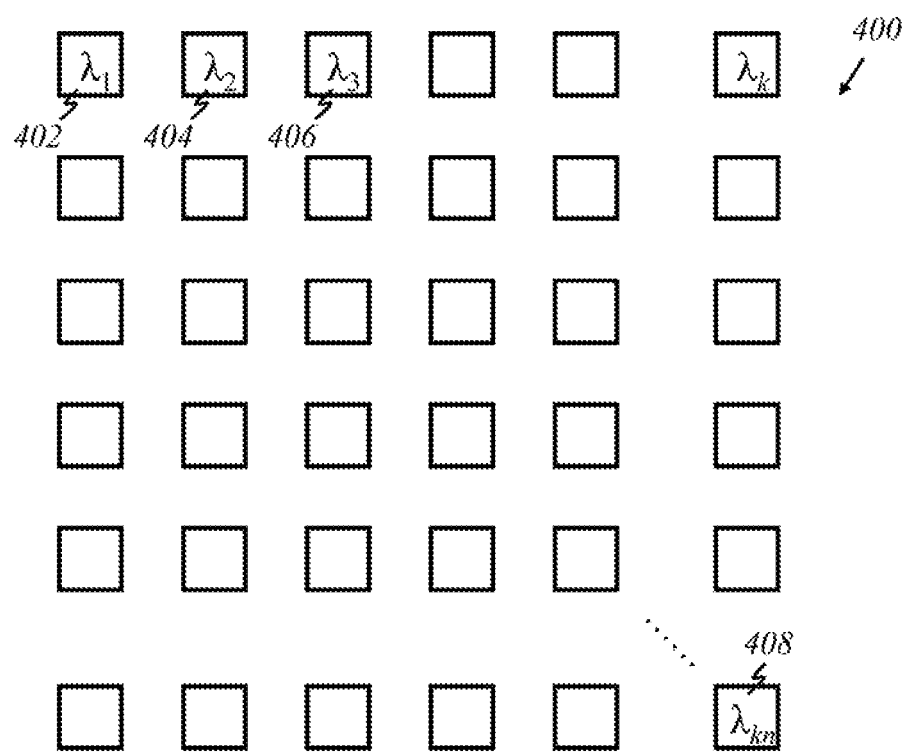
FIG. 3A Sources

Sources

Sources

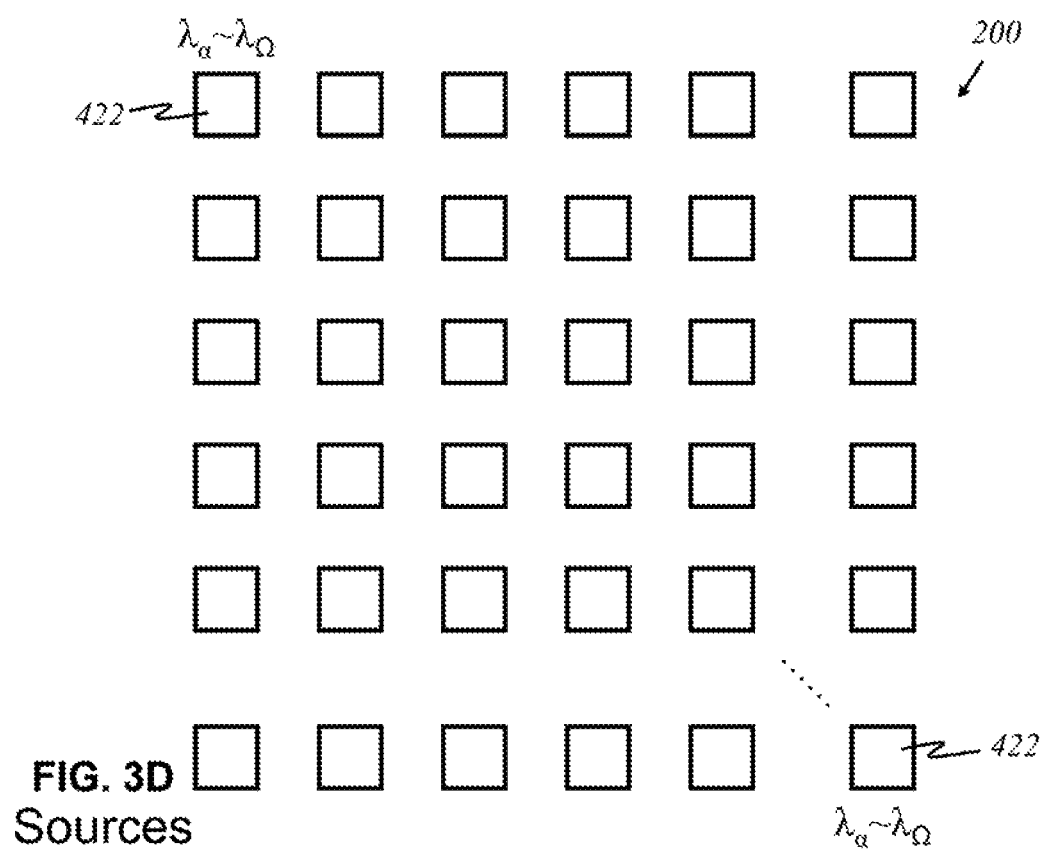
FIG. 3D Sources

Sources

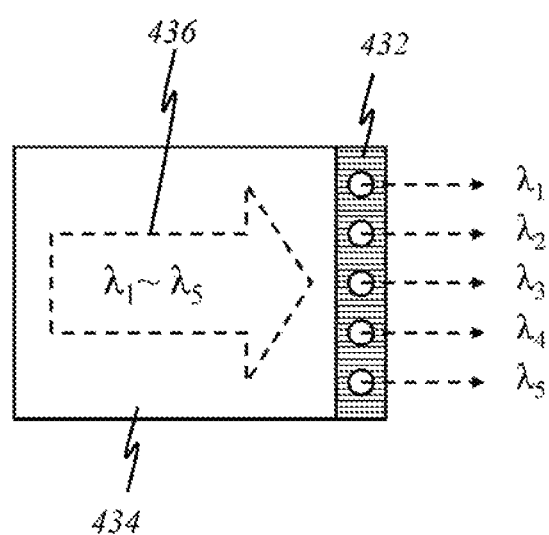
FIG. 3F Source w/ filter

Sources

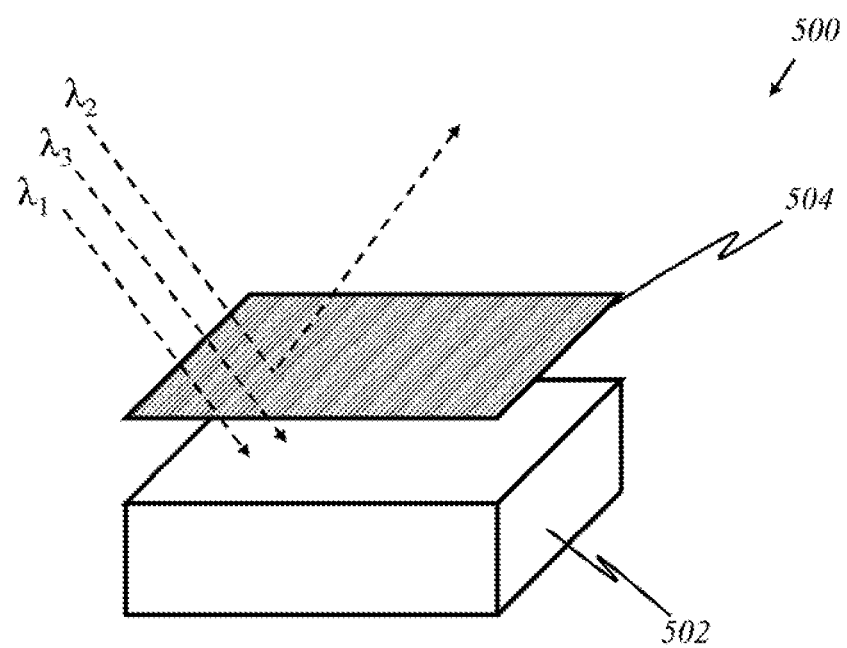
FIG. 4A Detector

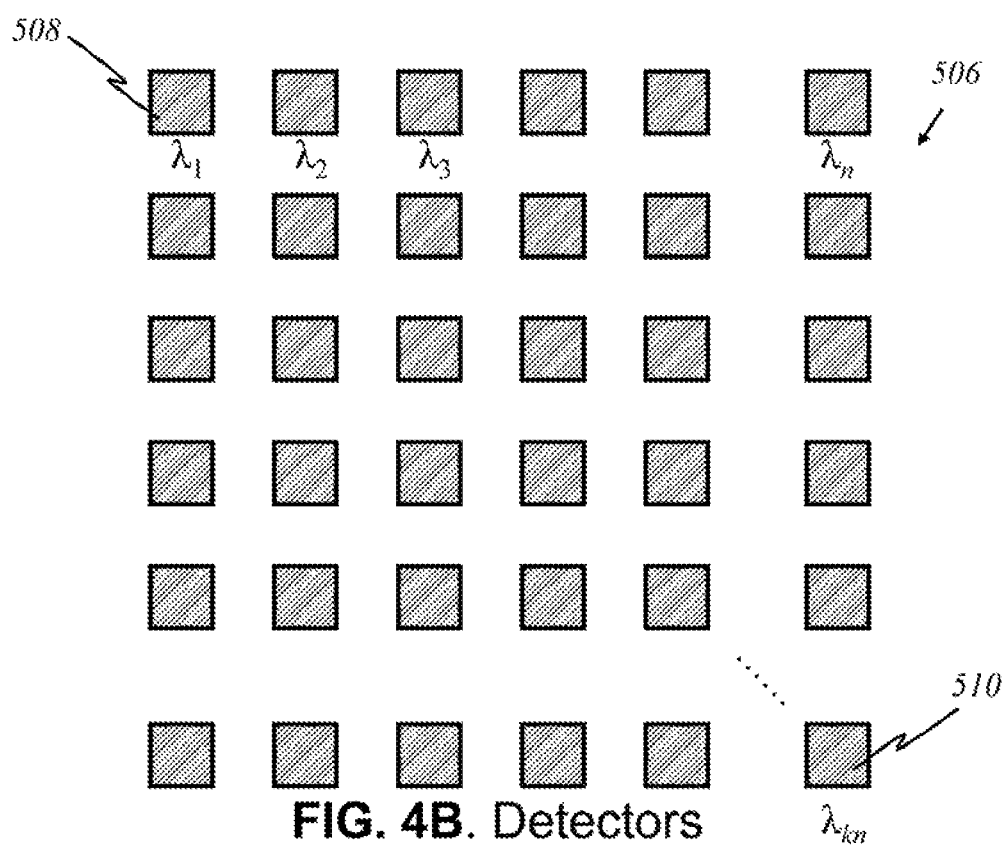
FIG. 4B. Detectors

Detectors

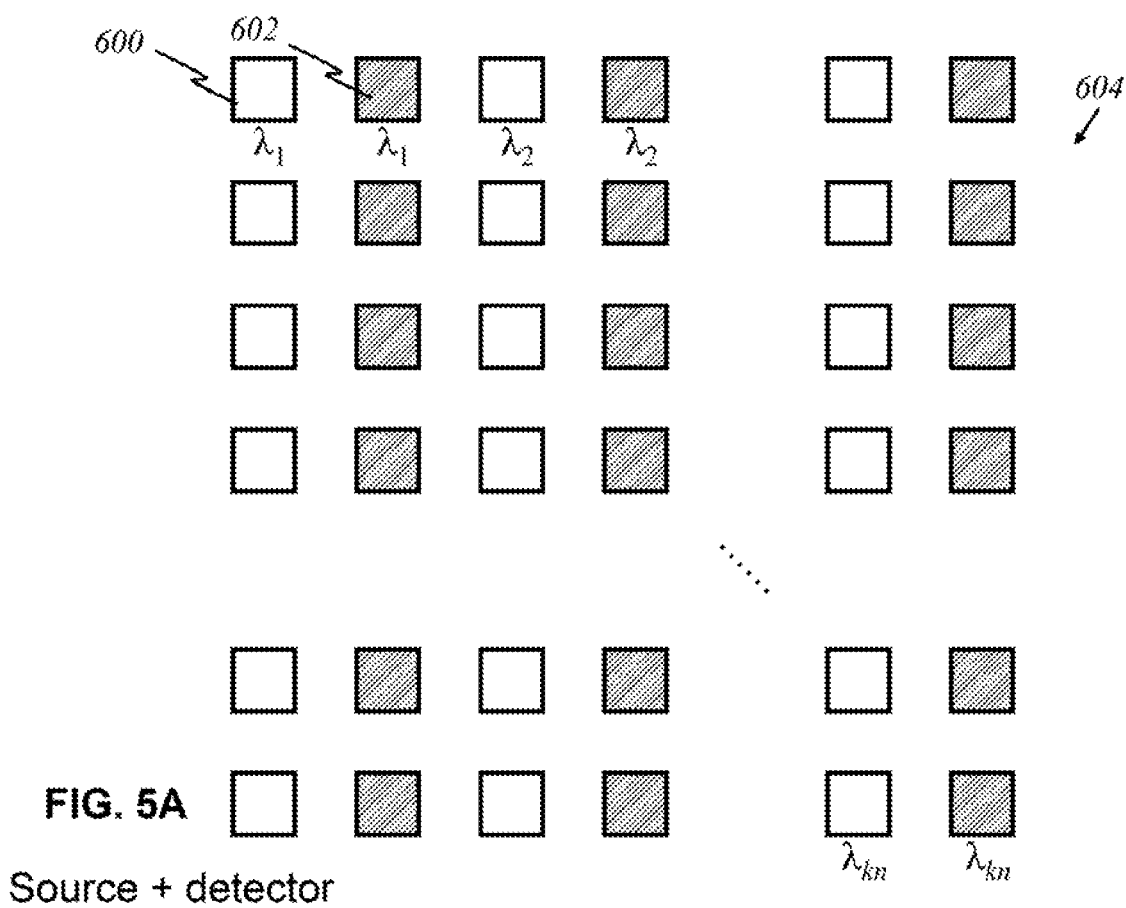

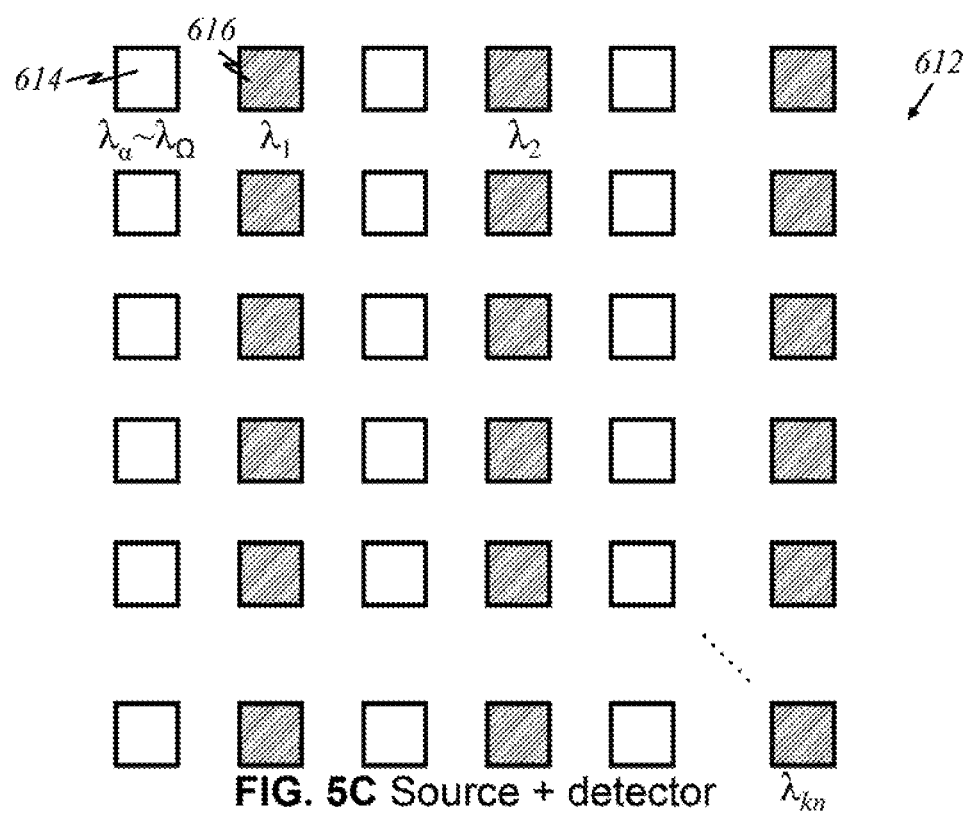
FIG. 5C Source + detector

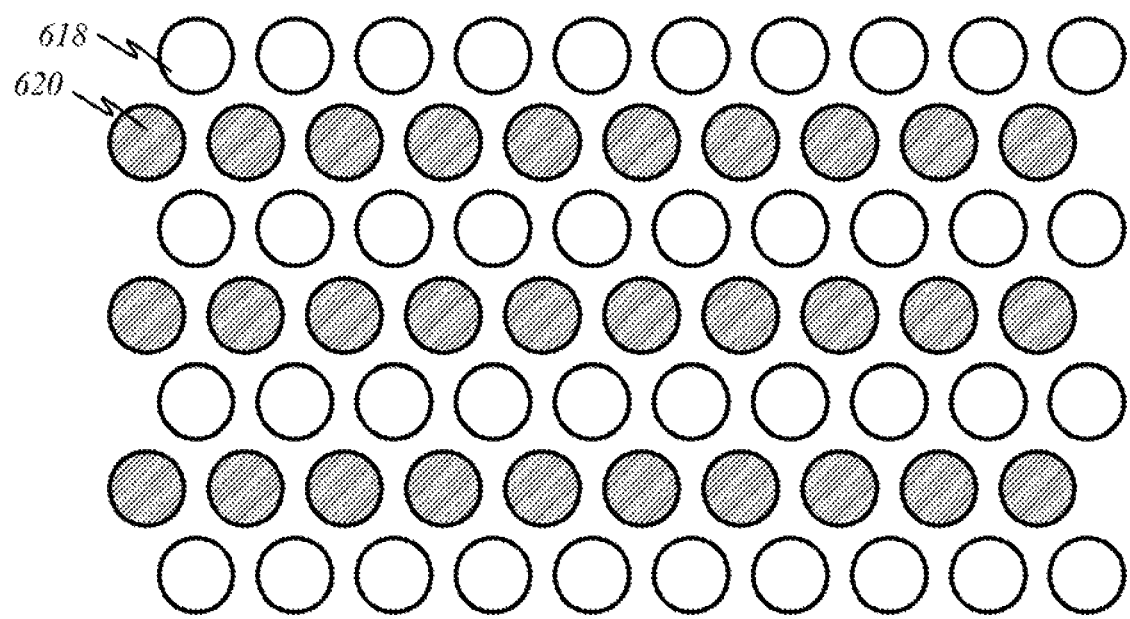
FIG. 5D Source + detector

*Angled view of wearable device*

*Possible top/bottom view of wearable device*

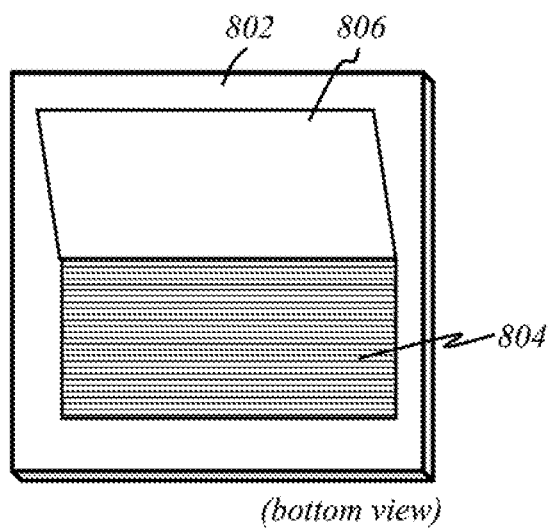 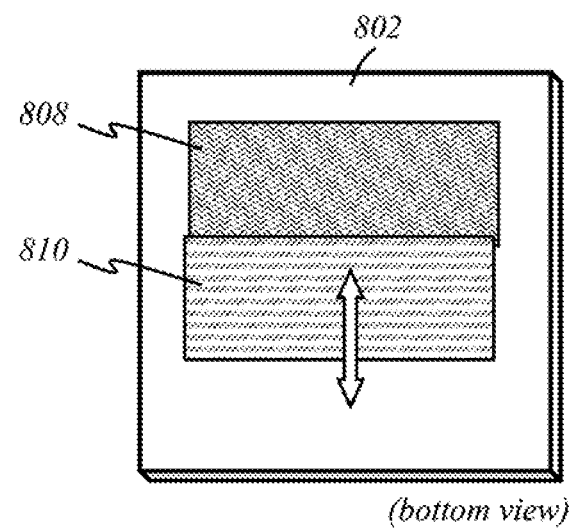
FIG. 7C  FIG. 7D
*Possible bottom view of wearable device*

*Close-up view of nano-bumps*

*Non-sweat type*

*Non-sweat type*

*Non-sweat type*

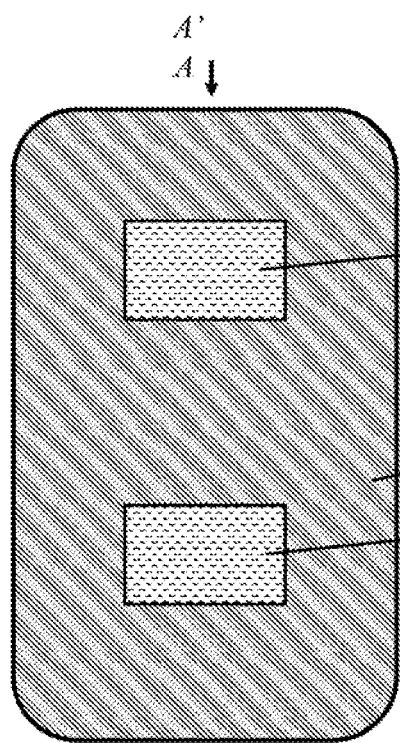
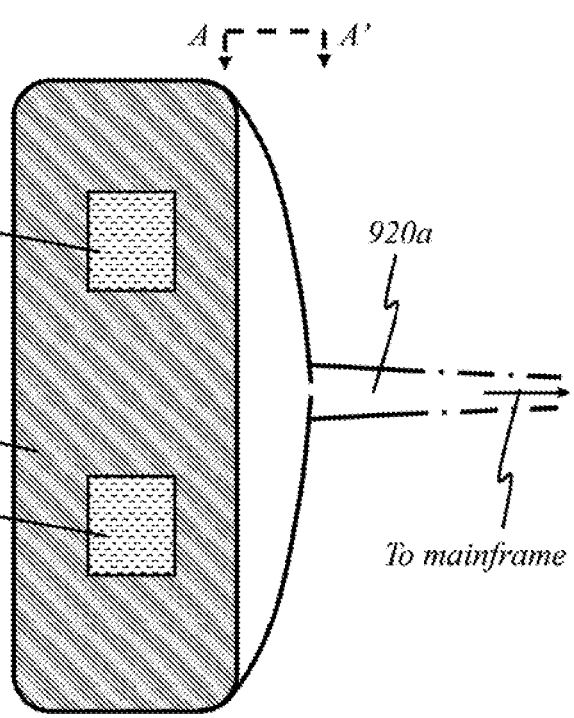
FIG. 8D  FIG. 8E

*Non-sweat type*

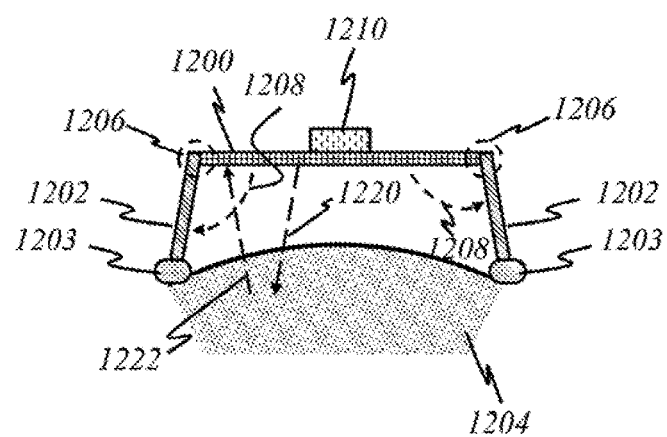
FIG. 11A Cross-sectional top view of non-contact, flip-open embodiment

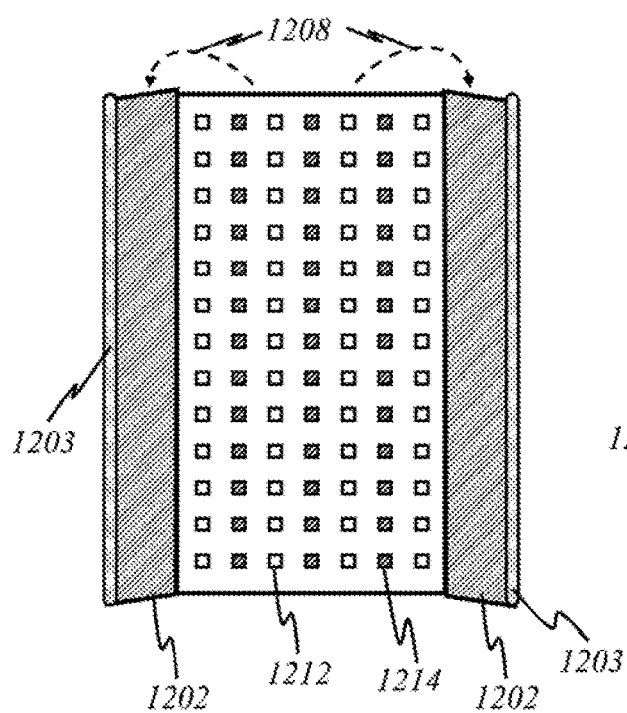 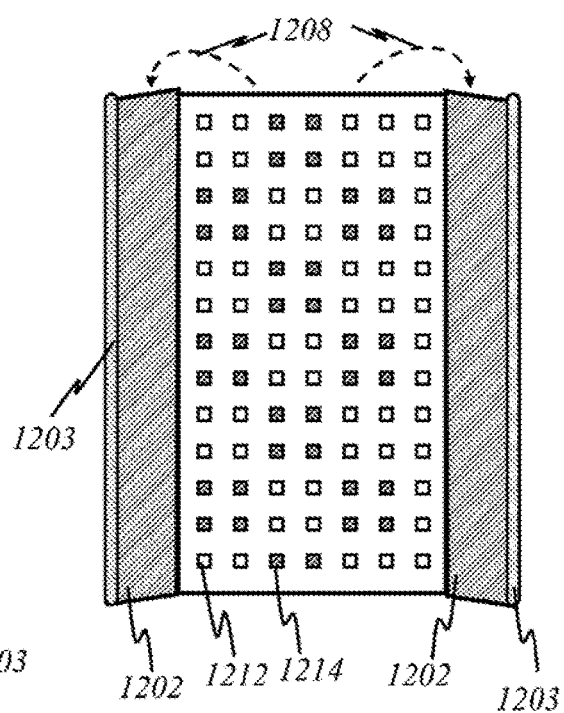
FIG. 11B  FIG. 11C
*Front view of flip-open embodiment (1)*

Cross-sectional top view of non-contact, flip-open embodiment with shields

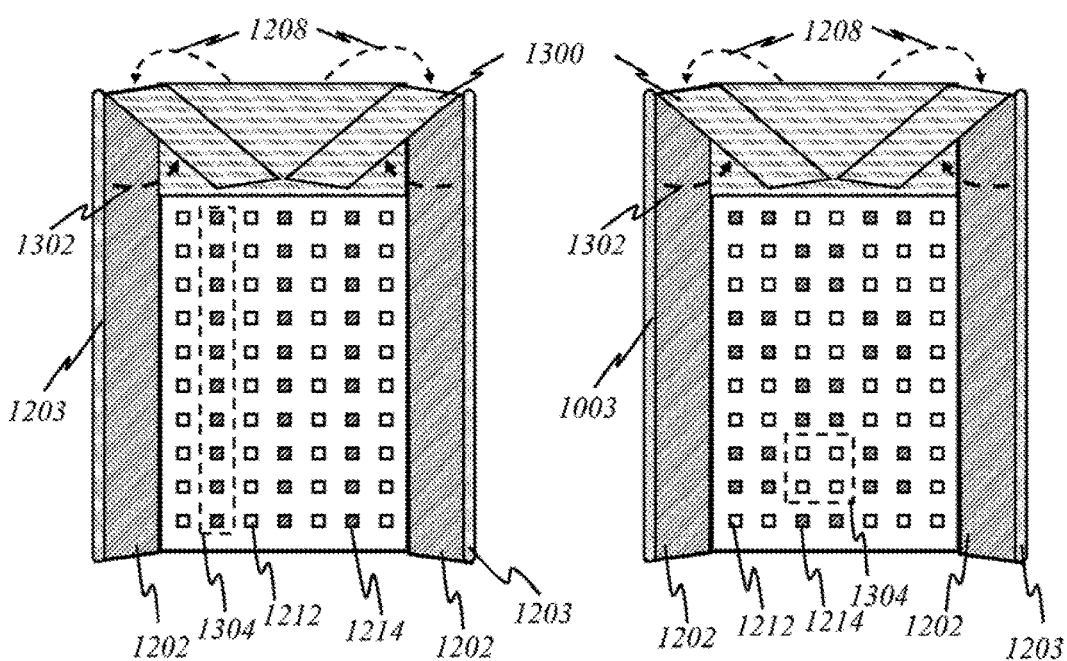
FIG. 12B  FIG. 12C
*Front view of flip-open embodiment (1) with shields*

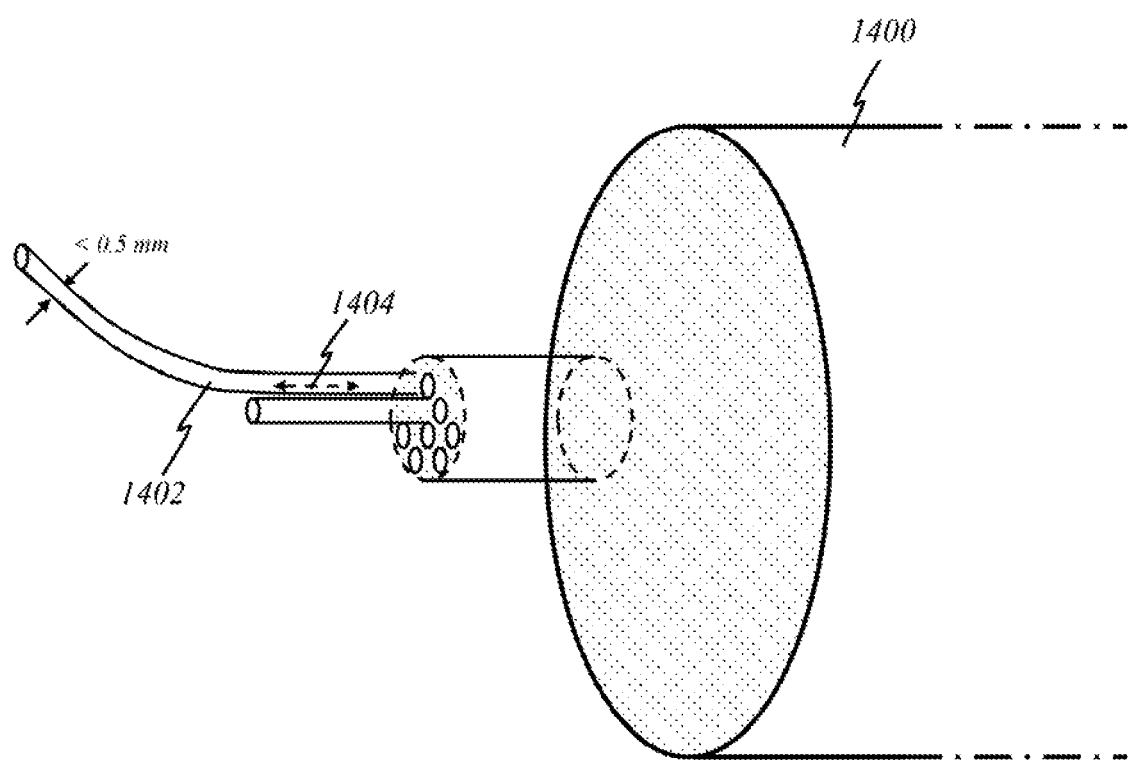
FIG. 13 Optical-fiber cable

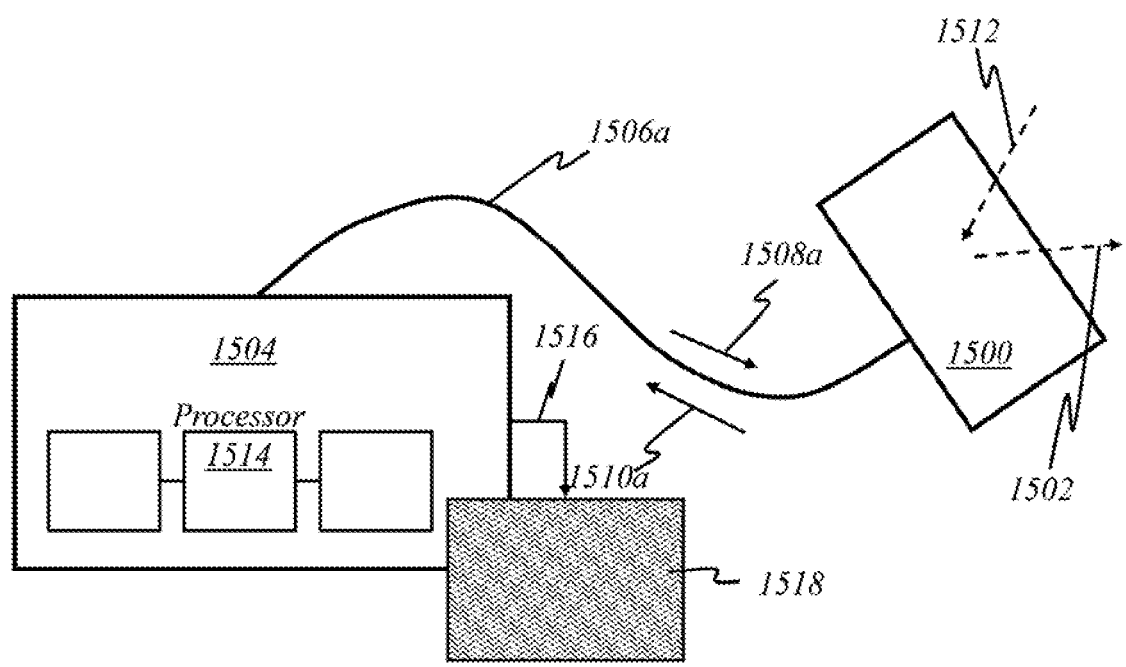
FIG. 14 Whole view (general schematic diagram)

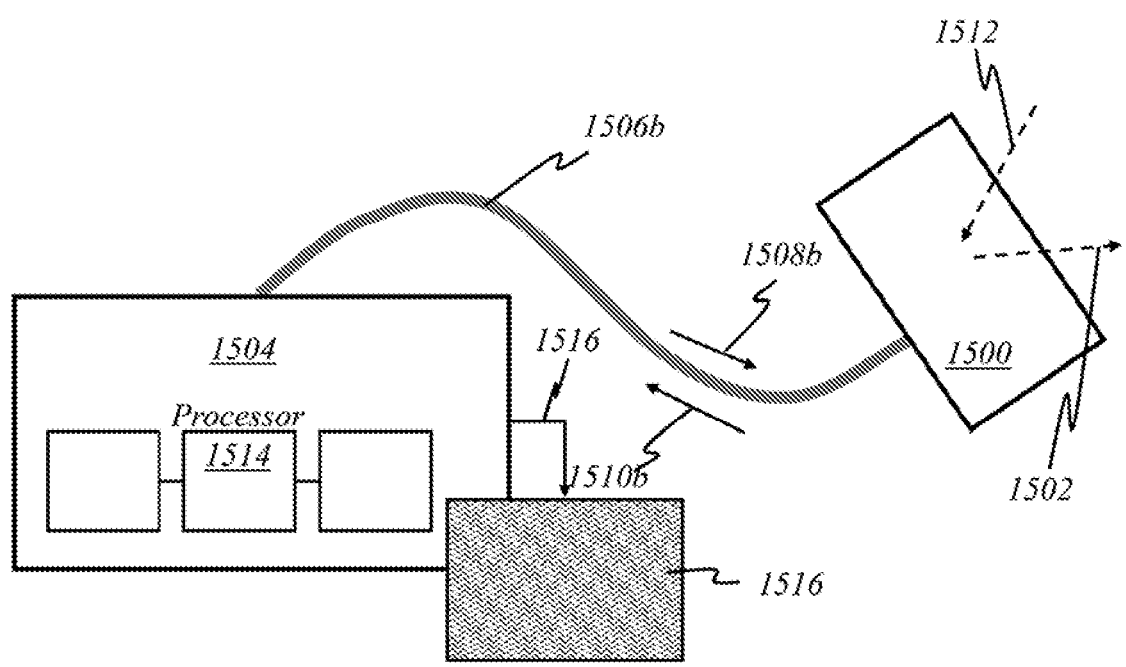
FIG. 15 Whole view (with electrical wire)

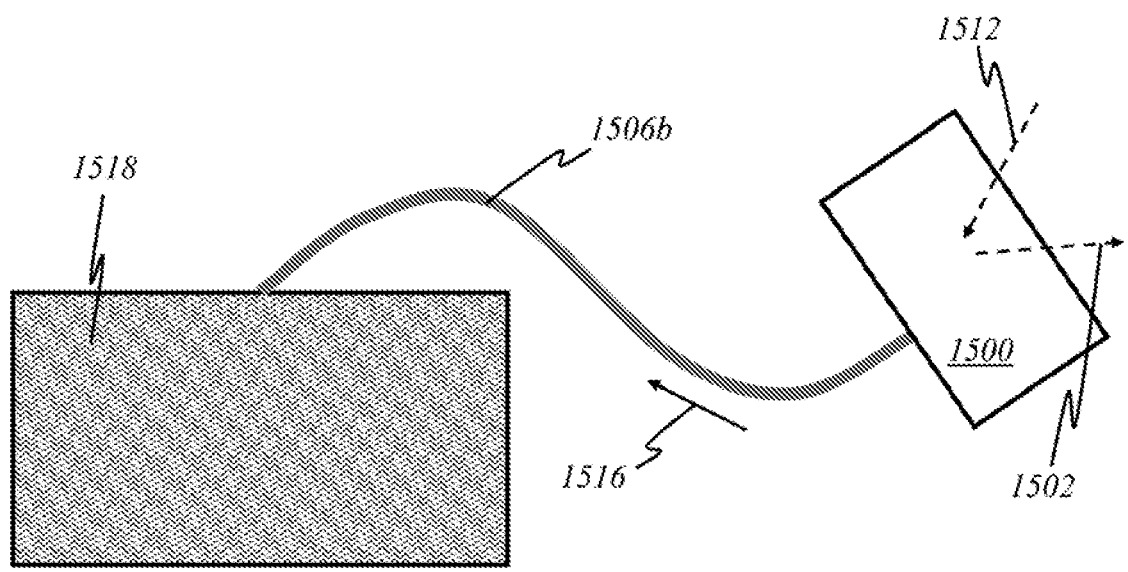
FIG. 16 Whole view (2) (with electrical wire)

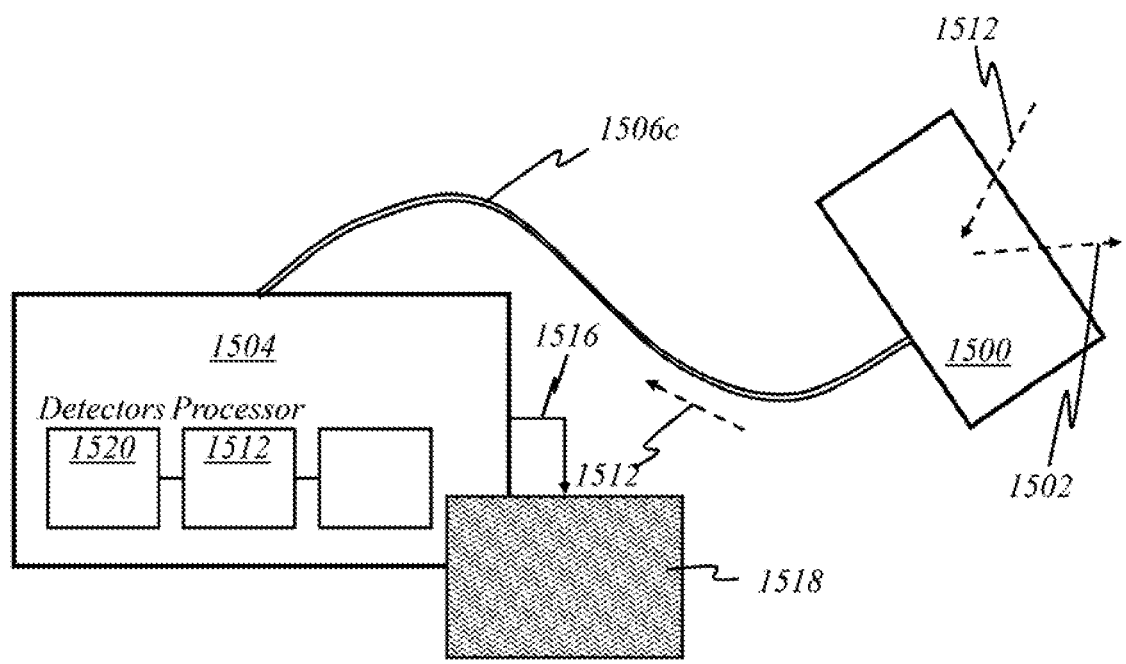
FIG. 17 Whole view (with optical fiber) (1)

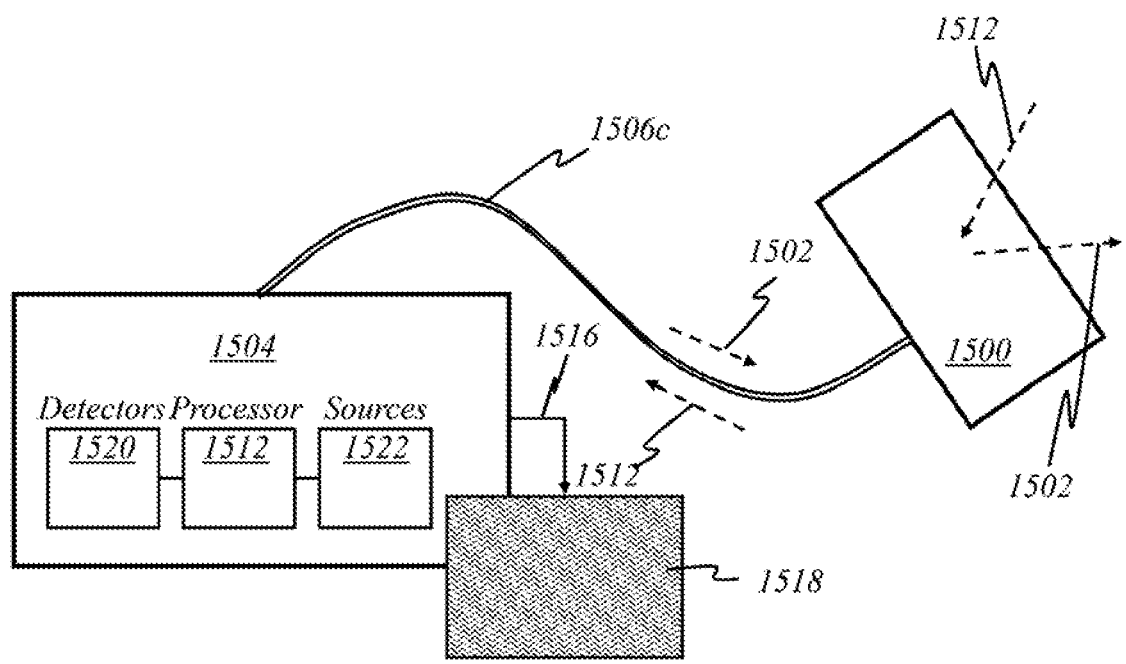
FIG. 18 Whole view (with optical fiber) (2)

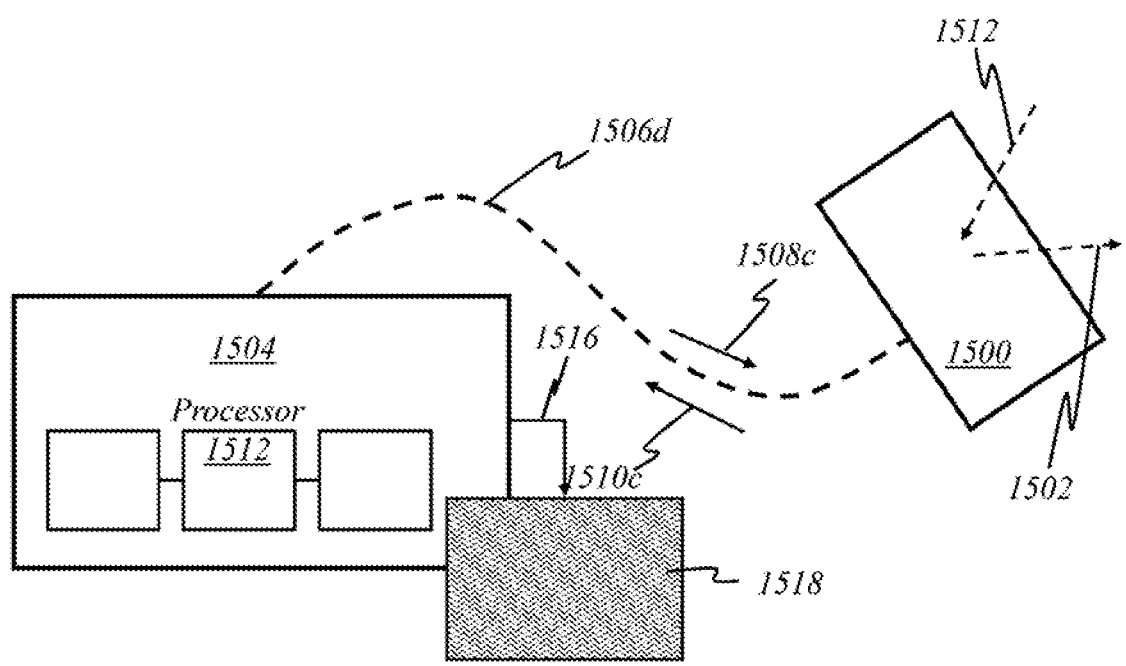
FIG. 19 Whole view (without wire)

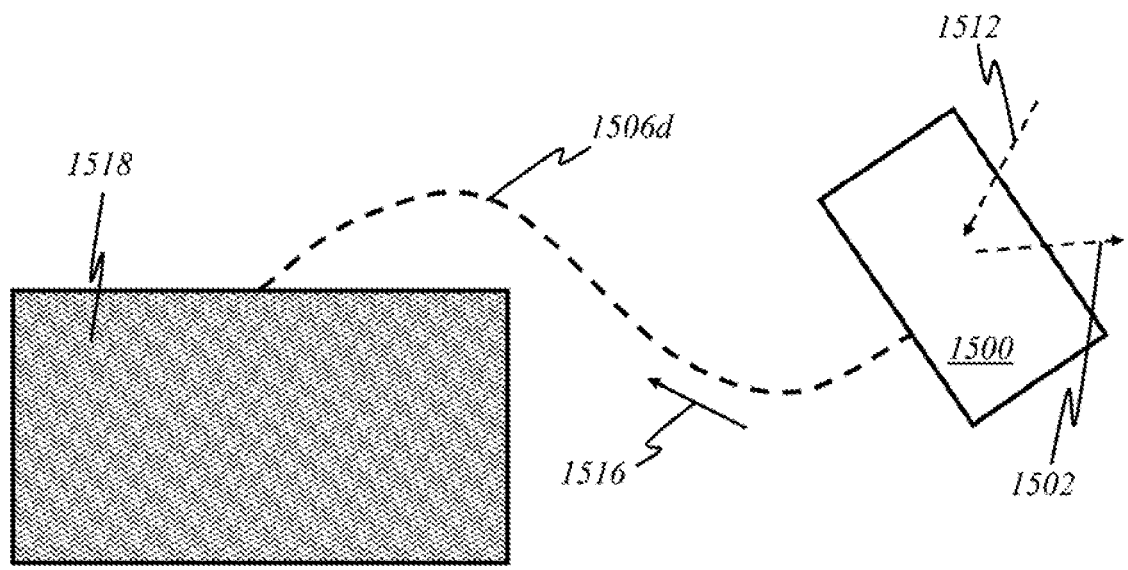
FIG. 20 Whole view (2) (without wire)

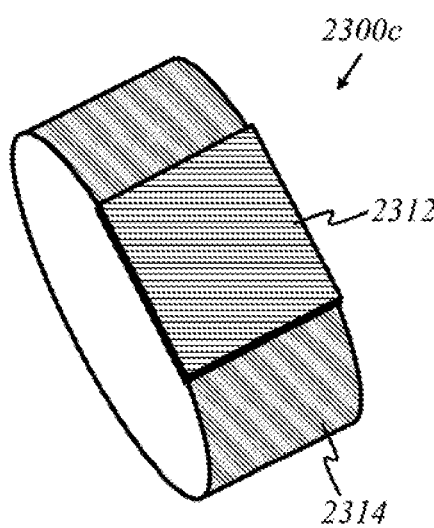
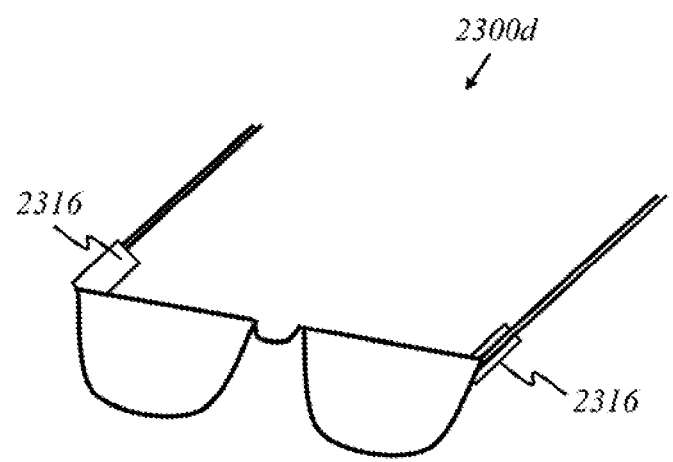
FIG. 22C  FIG. 22D

SYSTEM FOR SCREENING AND DIAGNOSIS OF DIABETES

FIELD OF THE INVENTION

This invention relates to the means for detection of molecular and chemical matter utilizing multiple techniques covering electronics, optics, and imaging techniques. More particularly, this invention is related to detecting levels of certain molecules inside the body through non-invasive contact or non-contact with the body. More specifically, this invention is related to the means to detect levels of molecules associated with metabolic diseases, more particularly the early diagnosis of the disease, especially diabetes. This invention also relates to a medical device that emits electromagnetic waves of varying wavelengths and detects waves returned to the device.

BACKGROUND OF THE INVENTION

Diabetes affects more than 20 million Americans and is a group of diseases that result from the body's inability to produce or use insulin A person suffering from diabetes usually has an excess of glucose in their bloodstream. Either the pancreas does not produce enough insulin (type 1), or cells do not respond normally to insulin that is produced (type 2). Insulin is the protein hormone responsible for regulating carbohydrate and fat metabolism in the body by moving glucose (sugar) from the bloodstream into cells, where glucose is then either used as fuel or stored for future use. There is no cure for diabetes, and individuals with diabetes must learn to monitor and control the amount of blood sugar in their bloodstream. Management of chronic diabetes is based on maintaining blood sugar levels close to normal amounts, which can be done by appropriate insulin or medication dosing, diet and exercise.

In the short term, diabetes can cause nonketotic hyperosmolar coma and diabetic ketoacidosis, which can lead to death. In the long term, complications include doubled risk of cardiovascular disease, chronic renal failure, diabetic neuropathy (disease of the nervous system), and diabetic retinopathy (retinal damage). It can create socioeconomic burdens as well: Diabetic patients with neuropathic symptoms such as numbness or tingling in feet or hands are twice as likely to be unemployed as those without the symptoms. Type 1 diabetes, also known as juvenile diabetes, is usually diagnosed in children and young adults. It is a rare type, diagnosed in 5% of people who have diabetes, that results from the body's failure to produce insulin. Type 2 diabetes is the most common form of diabetes, caused by insulin resistance, a condition in which the body does not use insulin properly. The body is eventually unable to maintain its efforts to produce extra insulin to make up for the insulin resistance. Prediabetes is a condition in which one's blood glucose is higher than normal but not high enough to be considered diabetes. Prediabetes puts one at risk for developing type 2 diabetes and can be a predictor for diabetes.

Detecting and treating diabetes early can decrease the risk of developing complications. However, expecting or detecting diabetes can be a challenge. Some people with type 2 diabetes have symptoms that are so mild that they are unnoticed. Even more latent, women who have never had diabetes may be at risk when they are pregnant. Many women whose pregnancy is approximately 24 weeks in develop gestational diabetes despite not having any diabetes before pregnancy, and it can lead to development of type 2 diabetes. Women with gestational diabetes often show no symptoms. There are several other major risk factors: older age, sex (twice as likely for males to have undiagnosed diabetes), genetics, ethnicity, high blood pressure, lack of physical activity, body weight. Therefore, it is important to encourage those who are at risk to test for diabetes often.

Currently, there are several ways to diagnose diabetes. Many factors affect the amount of glucose present in blood, and a person's blood glucose level will change throughout the day, usually reaching a low point before a meal and a high point after a meal. Therefore, when testing for glucose levels in the blood, it is often necessary for patients to fast for eight hours before the test in order to eliminate this variability.

The hemoglobin A1c (HbA1c, glycated hemoglobin) test measures a patient's average blood glucose for the past six to twelve weeks. There is no fasting involved nor intake of fluids required to perform the test. Although patients may use a small needle in a home kit to take a blood sample, the blood must be sent to a lab for testing. Otherwise, the patient may need to visit a doctor or lab personnel who have blood-analysis equipment. Generally, an HbA1c of at least 6.5% is consistent with diabetes; levels between 5.7% and 6.4% indicate prediabetes. However, results of A1c tests that are read at different labs vary, and patients with other abnormalities such as anemia, high cholesterol levels, or vitamin supplements may interfere with test results. Thus, it is not the most accurate method of diagnosing diabetes.

The oral glucose tolerance test (OGTT) provides insight into the ability of a patient's body to process glucose. The American Diabetes Association recommends all pregnant women not already diagnosed with diabetes use the OGTT to check for gestational diabetes. The test checks a patient's glucose level by taking a blood sample before the patient drinks a liquid containing a high amount of glucose, which may cause the patient to vomit and invalidate the test. As physical activity may interfere with results, the patient cannot move while the test progresses. The patient must also refrain from eating, drinking, smoking or exercising at least eight hours before the test. Blood glucose is measured again at intervals of one to three hours after the intake of the liquid. Different labs use different standards for determining diabetes based on the glucose levels at each interval.

The fasting plasma glucose (FPG) test checks a patient's blood glucose levels after fasting for at least 8 hours. It is the most preferred test for diagnosing diabetes. OGTT is more sensitive than the FPG test; however, the FPG test is more convenient to administer. Diabetes is diagnosed at fasting blood glucose of at least 126 mg/dl; prediabetes is diagnosed at fasting blood glucose between 100 and 125 mg/dl. Casual or random plasma glucose test checks the blood at any time when a patient shows diabetes symptoms, such as blurred vision, increased urination, increased thirst, or unexplained weight loss. Diabetes is diagnosed at blood glucose of at least 200 mg/dl. A method that is quick, non-invasive and convenient is needed for those who are at risk and wish to diagnose themselves regularly.

For patients diagnosed with diabetes, physicians may advise them to monitor their blood glucose levels at home as the best way to maintain control over their diabetes. This enables the patient to take immediate action if blood sugar levels are too high or low, as well as monitor the effect of medications and other factors such as diet, exercise, illness or stress. How frequently a patient must monitor their blood sugar level depends on the type of diabetes and the treatment plan prescribed by the physician. Finger-stick measurements are the most common technique used to monitor blood glucose level. Patients must prick a finger to obtain a blood sample, place the blood sample on a test strip, and then insert the test strip into a hand-held device which analyzes the level of glucose in the blood sample. For patients who require multiple tests per day, this becomes expensive, embarrassing, inconvenient and painful, especially for children, having to prick their finger multiple times a day, often in public. Compliance is a major issue with self-monitoring, with over 60% of type-1 patients not testing their blood glucose levels every day. A way for patients to monitor their glucose level at home that does not require taking a blood sample and does not use consumable parts is needed.

One method of non-invasive blood glucose measurement involves using near-infrared light (NIR) and spectral analysis. A biological sample is illuminated with a light source, reflected light is collected with a detector and the resulting spectral data is analyzed to determine glucose level in the blood. However, the accuracy of this technique is suspect because of the presence of other components in the biological sample. These other components, which include skin, fat, muscle, bone, and interstitial fluid, may influence the measurement and give an inaccurate reading. One particular problem is that any reading may take into account the glucose present in the other components, resulting in an inaccurate, higher glucose measurement. While the invention does try to account for these components using various models and calibrations, the amount of variation from person-to-person still remains problematic. Even accounting for such differences between people, variation of these factors between different measurement sites still remain.

Another non-invasive technique for measuring glucose levels has begun development, and a device using such a technique is the GlucoWatch. The device is first calibrated by taking a blood sample in the traditional finger-stick method. Once calibrated, the device draws interstitial fluid up through the skin and into the device using a small electrical current and measures the glucose level in the fluid. It takes a measurement every ten minutes for up to thirteen hours, allowing individuals to detect and track patterns in glucose levels. However, this device is not truly non-invasive because it still requires a blood sample for calibration. It also requires two hours to warm up before use, and users report skin irritation. In addition, the device is not recommended for solo use and should be used in conjunction with the traditional finger-stick measurements because of the risk of inaccurate readings. It has been reported that 25% of readings will vary more than 30% from the actual blood sugar level.

One of the few advantages of finger-stick measurements is the ability to take accurate measurements with little regard to the conditions of use. Because the measurement is taken from the blood directly, little attention needs to be given to the variability of external factors. These factors include but are not limited to, temperature, bumping or excess movement, sweating, and skin thickness. For example, the GlucoWatch has reported skipping readings with the presence of sweat or cold skin. Therefore, any non-invasive device for measuring blood glucose levels must be able to overlook these challenges.

Glucose can be measured in many different body fluids, not just the blood. Glucose is also present in interstitial fluid, aqueous humor, vitreous humor, lymph, urine, sweat, saliva, tears, and cerebrospinal fluid. However, measurements taken from the blood is considered the "gold standard" in measuring glucose because it is the most direct. Results from a blood glucose test directly reflect the amount of glucose in the blood, whereas measuring the amount of glucose in other fluids is indirect because glucose is present in these other types of body fluids only after diffusing out of the blood. Therefore, there is a time delay problem associated with measuring the glucose level in these other fluids because it may take several hours for glucose level in tears or saliva to accurately reflect the glucose level in the blood. Out of these other fluids, interstitial fluid (ISF) has the most potential as an alternate means of glucose measurement because it has the shortest time delay; some studies have even shown that there is no time delay at all. Taking measurements using any of these fluids may still be a helpful indicator, especially if taken in combination.

It would be useful and desirable to have a portable, convenient, and non-invasive device that anyone at risk can use to screen themselves for diabetes or monitor their blood glucose frequently and at any time without the need to rely on ambiguous symptoms, physiological stress from fasting or spiking the body's glucose levels, invasive blood-drawing procedures, or inconvenient visits to physicians or laboratories. The present invention seeks to present a non-invasive device capable of measuring glucose levels using multispectral imaging and in multiple types of bodily fluids for increased accuracy. The present invention provides a compact, portable device that uses multispectral imaging to assess the concentrations of biological molecules as well as determine potential development of diabetes with increased accuracy. Rapid and recurring delivery of relevant results in the privacy of one's home allows the user to interpret the results and decide whether to invest further time and energy by visiting a physician, who can answer questions and explore treatment and prevention options before prediabetes or diabetes worsens. Alternatively, those who are chronically afflicted and need to maintain euglycemia can manage their blood glucose levels non-invasively.

SUMMARY OF INVENTION

The present invention aims to overcome problems associated with current technologies by providing a method and device that makes management and diagnosis of diabetes more accurate, less invasive, less costly, and more amenable to routine self-examination.

The following presents a summary of the invention and a basic understanding of some of the aspects of the invention. It is not intended to limit the scope of the invention or provide critical elements of the invention. Its sole purpose is to present some of the features of the invention in a simplified form as a prologue to the more detailed description presented later.

It is an object of this invention to allow diabetes diagnosis and blood glucose maintenance to be non-invasive.

It is an object of this invention to encourage routine diabetes diagnosis for people with risk factors. (Lower cost, easier access, more private, self-serve.)

It is an object of this invention to raise the accuracy of diagnosis and readings and reduce the rate of false positives and false negatives.

BRIEF DESCRIPTION OF DRAWINGS

For a better understanding of the aforementioned aspects of the invention and additional aspects and embodiments thereof, reference should be made to the Detailed Description, below, in which reference numerals refer to corresponding parts throughout the figures under Drawings.

FIGS. 1A and 1B show a cross-sectional view and a top view, respectively, of an electronic circuit activated by the presence of charged ions.

FIG. 1C shows a cross-sectional view of a nano-membrane, a component of the circuit of FIGS. 1A and 1B.

FIG. 2 shows a block diagram illustrating the basic operational parts of the present invention.

FIGS. 3A-3G show various arrangements of light sources that may be implemented in accordance to the present invention.

FIG. 4A shows a schematic of basic parts of a light detector.

FIGS. 4B and 4C show various arrangements of detectors that may be implemented in accordance to the present invention FIGS. 5A-5E show various arrangements of sources and detectors that may be implemented in accordance to the present invention.

FIGS. 7A-7D show top and bottom views of possible embodiments and functional parts of a device that detects metabolites electronically or optically according to the present invention.

FIGS. 8D and 8E show a front view and an angled view, respectively, of the device of FIGS. 8A-8C.

FIG. 11A shows a schematic of a "non-contact" embodiment in a top view.

FIGS. 11B and 11C show schematics of the "non-contact" embodiment in a front view.

FIGS. 12B and 12C show schematics of the "non-contact" embodiment of FIG. 12A in a front view.

FIG. 13 shows a schematic of an optical-fiber cable used in the present invention.

FIGS. 14-20 show a whole view of schematics of operational parts implemented in preferred embodiments of the present invention.

FIGS. 22A-22D show schematics of the present invention implemented in various example devices.

DETAILED DESCRIPTION OF THE INVENTION

Figure 3B:
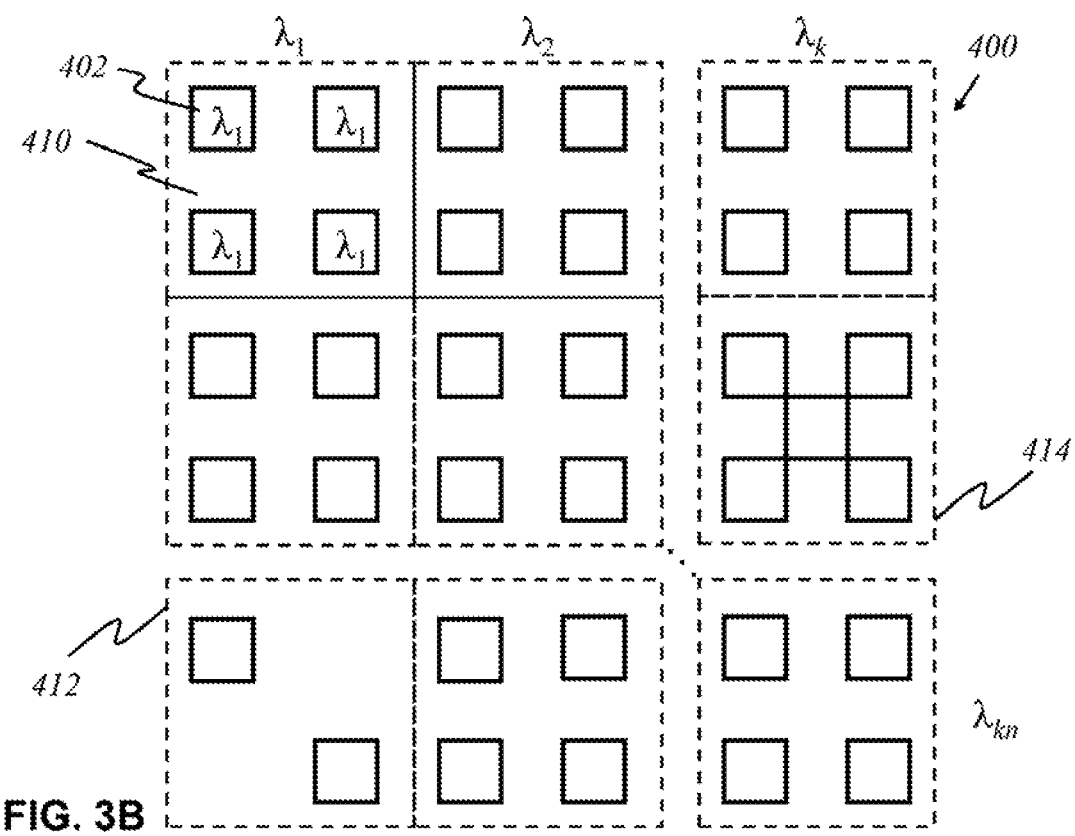

Reference numerals refer to corresponding parts labeled throughout the figures. The embodiments described herein pertain to detection of concentrations of molecular and chemical matter in bodily fluids through optical techniques. The embodiments pertain to methods and apparatuses for screening and diagnosis of diabetes.

As used herein, the term "component of interest" refers to ions and small molecules that exist inside bodily in different amounts and concentrations under different conditions. Examples include hydrogen ion ($H^+$), carbon dioxide ($CO_2$), glucose, insulin, and hemoglobin. Other components may become apparent in the description that follows.

As used herein, the term "biomass" refers to a total mass or volume of organic matter, typically from the human body. It could be an entire organ or portion thereof, a section of skin, lymph or blood vessels present throughout the body, and/or a collection of cells, ex vivo or in vivo. In the present invention, discussion of "biomass" is aimed primarily near the surface of the skin, blood vessels, lymph vessels, vitreous humor, and other parts of the body where indicators of diabetes, e.g., glucose, can be found.

As used herein, the term "metabolite" refers to a substance produced by biological metabolism in the user's body, especially molecules and charged ions such as glucose, insulin, carbon dioxide ($CO_2$), water, hydrogen ion ($H^+$). These are examples of "metabolites" that indicate internal symptoms pointing to the onset or presence of diabetes. A combination of these factors increases the likelihood of onset or presence of diabetes.

As used herein, the terms "light," "radiation," "electromagnetic wave" and "electromagnetic waves" are interchangeable, unless specified. "Broadband" light refers to light carrying waves of varying wavelengths, typically a range of wavelengths (or a band). Broadband light is generated by a broadband source, which may emit multiple ranges of wavelengths to selectively emit multiple groups of wavelengths. On the other hand, "uniband" or "coherent" light refers to light having one particular wavelength or a narrow range of wavelengths.

As used herein, the terms "noninvasive" and "invasive" refer to whether the skin is pierced, cut, incised, or penetrated by macroscopic solid matter. Penetrating of the body, as by incision or injection, is "invasive," while using light or radiation to infer the content under the skin is "noninvasive" since there is no breaking or opening of the skin.

As used herein, the terms "reflect," "refract," "scatter," "diffract" and "fluoresce" refer to the behavior of light waves upon interacting with another material. "Reflect" refers to a process in which light and other electromagnetic radiation are cast back after impinging on a surface. "Total internal reflection" occurs when light strikes a medium boundary at an angle larger than a particular critical angle with respect to the normal to the surface. "Refract" refers to change in direction of electromagnetic radiation in passing from one medium to another. The optical density of a medium is the refractive index, an inherent value of the medium. "Fluoresce" refers to exhibiting fluorescence, which is refers to emission of electromagnetic radiation stimulated in a substance by the absorption of incident radiation. "Diffract" refers to exhibiting diffraction, which refers to a deviation in the direction of a wave at the edge of an obstacle in its path. "Scatter" and "diffract" are interchangeable.

As used herein, the term "panel" associated with light sources and light detectors refer to a continuous and generally transparent surface that emits or receives light. Multiple light source and light detector units are housed under a panel. This is distinguishable from a mere collection or array of sources or detectors. An array is an arrangement of sources or detectors, but each source or detector is discretely placed, not connected to one another or housed under one transparent pane.

The terminology used in the descriptions of the embodiments herein is for the purpose of describing particular embodiments only and is not intended to limit the claims. The singular articles "a," "an" and "the" are intended to include the plural forms as well, unless the context clearly indicates otherwise. It will also be understood that the term "and/or" refers to and encompasses any and all possible combinations of one or more of the associated listed terms. Similarly, the conjunction "or" is not necessarily mutually exclusive.

References will now be made in detail to embodiments, accompanied by numerals that correspond to appropriate parts of the figures. Examples will be provided to illustrate the various ways the present invention may be utilized. Specific details will be set forth to provide a thorough understanding of the present invention. However, it will be apparent to those with ordinary skill in the art that the present embodiments may be practiced without these specific details. In other instances, known methods, procedures and components have not been described in detail to avoid unnecessarily obscuring aspects of the embodiments.

In the normal respiratory process, carbon dioxide ($CO_2$), water, and carbonic acid ($H_2CO_3$) in the blood maintain an equilibrium. Diabetic ketoacidosis results from production of acidic ketones resulting from insulin shortage. In conditions where blood acidity rises—for example, increased production of metabolic acids, lower excretion of acid by kidney, hypoxemia, hypoperfusion, hypoventilation, and diabetes—the equilibrium shifts to carbon dioxide and water because equilibriums between carbonic acid and bicarbonate ($HCO_3^-$) and between bicarbonate and carbonate ion ($CO_3^{2-}$) shift toward increased concentration of carbonic acid. In other words, high blood acidity compensates for it via hyperpnea:

$$HCO_3^- \leftrightarrow CO_3^{2-} + H^+$$

$$H_2CO_2 \leftrightarrow HCO_3^- + H^+$$

$$CO_2 + H_2O \leftrightarrow H_2CO_3$$

Therefore, metabolic characteristic of a diabetic patient is, among others, increased expiration of $CO_2$, increased concentration of $H^+$ in the blood and bodily fluids, and increased concentration of glucose in the blood and bodily fluids (including exhaled respiratory fluids). These indicators can serve as multiple factors to increase reliability of detection of diabetes onset through ongoing monitoring of patients at risk. The greater the indicator of diabetes, the greater the recommendation to the user to seek diagnosis or treatment.

FIG. 1A is a schematic showing a cross-sectional view of an electronic circuit that is activated by the presence of charged ions. A substrate 100 includes a p-n junction with a p-doped semiconductor 102 and an n-doped semiconductor 104, between which lies a depletion layer 106. Each metal contact 108 makes contact with p-doped semiconductor 102 and n-doped semiconductor 104. Metal contact 108 is needed to connect a battery 110 to p-doped semiconductor 102 and n-doped semiconductor 104. In preferred embodiments, metal contacts 108 create near-zero resistance when contacting p-doped semiconductor 102 or n-doped semiconductor 104. The circuit is completed when electrons flow through p-doped semiconductor 102, depletion layer 106, n-doped semiconductor 104, metal plats 108, and wires 112. The resistance of depletion layer 106 depends on the concentration of ions in depletion layer 106. Between metal contacts 108 is a nano-membrane 114 that acts as a filter for materials that are at most in the nanoscaled range. Nano-membrane 114 may be a rigid material or it may be more flexible. It may be one continuous material including pores and channels, or may be a filter that restricts access to channels underneath (see FIG. 1C). Nano-membrane 114 allows in materials such aqueous fluids containing as charged ions to pass, but it resists entry of proteins, particles visible to the eye, and other such macromolecules.

FIG. 1B is a schematic showing a top view of an electronic circuit that is activated by the presence of ions. In this embodiment, nano-membrane 114 is positioned between metal contacts 108, below which are p-doped semiconductor 102 and n-doped semiconductor 104 (not shown here). Wires 112 may be embedded within, below, outside, or above substrate 100, connecting to battery 110 (not shown here). This circuit is on a micro- or nano-scale size that makes it amenable to integration with a larger circuit or a wearable device.

FIG. 1C is a schematic showing a cross-sectional view of an example nano-membrane 114. Along a surface 116 of nano-membrane 114, there may be particles that are too large and particles that are small enough to fit through channels 118. For example, a small molecule 120, such as glucose or other saccharides, as shown is too large to fit through nano-membrane 114. A macromolecule 122, such as a protein or lipid, as shown is also too large to fit through nano-membrane 114. However, a droplet 124 of aqueous fluid containing ions is composed of small molecules and is fluid enough to fit through channel 118. Conversely, the pores may be large enough for most molecules and microparticles to pass through. In this type of embodiments, the objective is to capture fluids containing components of interest, such as glucose, traces of $CO_2$ molecules, and traces of $H^+$ ions. The objective is not to filter materials by size because the sensory mechanisms on the other side of the pores and channels detects the presence of certain materials regardless of the presence of other components that are not of interest.

The sensitivity of the p-n junction may be adjusted by varying the semiconductors used in the n or p side to vary the resistance occurring between p-doped semiconductor 102 and n-doped semiconductor 104. Semiconductors including Si, Ge, III-V or II-IV compound semiconductors, polymer electronics may be used. In various embodiments, the sensitivity may reach in up to parts per million, parts per billion, or parts per trillion.

The resistance value of depletion layer 106 varies on presence of ions. The measurable resistance between p-doped semiconductor 102 and n-doped semiconductor 104 is related to the concentration of ions that move through nano-membrane 114 and reach depletion layer 106. By knowing the relationships between the resistance and the ion concentration, and measuring the resistance of depletion layer 106, the concentration of ions present can be derived.

FIG. 2 is a block diagram illustrating the overarching concept of the present invention. At time $t_0$, a light source 200 emits light 202 of a particular wavelength ("uniband") or varying wavelengths ("broadband") into a tissue (skin) 204. In some embodiments, each source 200 is lined up in a two-dimensional fashion to create an array of sources (see below). Each source 200 may emit a certain wavelength. In some other embodiments, sources emitting the same wavelength may be grouped into larger panels. In yet other embodiments, each source 200 may emit a range of wavelengths. A source driver 206 drives source 200 and selects the pulse duration to be operated. Source 200 can be operated in continuous wave (CW) or pulse operation based on the necessities, and it converts electric signals to optical signals. A controller 208 receives instructions to provide signals to a source driver 136, which operates a specific source. Alternatively, controller 208 also receives instructions to operate the sources having specific wavelengths and/or specific ranges of wavelengths in either pulse or CW operation. According to this invention, alternatively, controller 208 can be operated and are instructed by one or more circuit blocks (not shown here) to operate desired source, desired wavelength(s), desired pulse-width/CW, desired intensity, or a combination thereof.

Light 210 returns as a reflection, or scatters and comes back as diffracted, refracted, or scattered light. At time $t_1$, a detector 212 receives returned light 210 of a certain wavelength. Detector 212 converts light 210 into electrical signals, which are sent to a signal amplifier 214. A digitizer 216 turns the amplified signal into digital form. A processing element ("processor") 218 performs calculations that can create three-dimensional images from two-dimensional images. Processor 218 produces other important data. For instance, it determines the location of areas of concern by deriving times of flight $t_1$-$t_0$ and the size of areas of concern by comparing images from light of different wavelengths. Although some absorption of emitted light 202 occurs, if an object has a size smaller than the wavelength of light hitting it, diffraction and scattering of the light occurs. On the other hand, if an object has a size larger than the wavelength of light, the object reflects the light. Thus, processor 218 may determine the size of potential tumors by collecting images based on light 202 of varying wavelengths. Processor 218 then sends relevant information to a display screen 220 for a user to read.

According to this preferred embodiment, processor 218 operates the transmission elements and the receiving elements (not shown here specifically), and processes the receiving signals based on a build-up algorithm, described later. The transmission elements (not shown here specifically) comprise controller 208, driver 206, and source 200. Processor 218 instructs the transmission elements and receiving elements, based on its determination of how to operate the source and which part of receiving elements should be processed.

By way of example and without any limitation, in FIG. 2, the source can be operated in various ways using blocks ("components")? having the functionality to select the source, wavelength, pulse/CW, and source intensity, and in various ways processor 218 can operate the transmitter elements and receiving elements, as instructed by software, either embedded into processing unit 218, and/or separately operated by a computing unit with or without display element 220 externally interfaced with processor 218.

According to this invention, alternatively, the components as shown in FIG. 2 may be grouped in different locations. The dotted lines above the block diagram indicate how the components may be grouped together. In some embodiments (Embodiment A), light sources 200 and detectors 212 are placed together in a handheld device separate from the module containing processor 218 along with the other components illustrated. The handheld device is henceforth referred to as the "user end"; the latter module is henceforth referred to as the "processor end". During operation, the user directly manipulates the handheld "user end" device over a patch of skin, emitting light 202 and detecting returning light 210. Light 210 that returns to the user end is sent to the processor end (containing processor 218) through electrical, optical, or wireless channels. The transmitted signals are then amplified, processed, and may be displayed on screen 220.

According to this invention, in some other embodiments (Embodiment B), light sources 200, detectors 212, and processor 218 are in the processor end. Initial emission and later collection of light are both performed at the processor end. Light 202 emitted from sources 200 and light 210 returned to the detectors 212 propagate through an optical-fiber cable. At the other end of the optical cable is a handheld device on the user end, which the user places, moves, or otherwise manipulates over tissue 204. This device delivers light 202 emitted and carried via optical means from sources 200, and then collects and focuses returned light 210 for transmission back through the optical cable to detectors 212. Electrical or wireless means are not used in these embodiments because only optical signals travel between the user end and the processor end.

In yet other embodiments (Embodiment C), light sources 200, detectors 212, and processor 218 are in one device: the user end. All light generation, data gathering, processing, and imaging are done within the handheld device. End result of operation, such as images and other data, are transferred via electrical, optical, or wireless means to display screen 220 or another device, such as a mobile device or a monitor of a computer. Other means of implementation and descriptions of accompanying figures are disclosed below to reveal a closer look at the arrangements of sources 200 and detectors 212.

A diffraction pattern, i.e., an interference pattern that propagates uniformly when a wave or a series of waves undergoes diffraction, results if an obstacle has a size smaller than the wavelength of optical wave encountering the object. The pattern provides information about the frequency of the wave and the structure of the material causing the diffraction. An interferometer can be used to detect the nature of the diffraction pattern.

Functions of above-described embodiments of the handheld device are driven by software programs. There are several main functions, including optically measuring the concentration of glucose in the blood and electronically detecting certain ions and molecules. Optical parameters include wavelength, energy fluence rate (flux over time), pulse rate, absorption coefficient, scattering coefficient, refractive index, scattering phase function. Light propagation in scattering and absorbing media can be defined with respect to radiative transfer.

According to one-dimensional transport theory, light propagation in scattering and absorbing media can be defined by integro-differential equation of radiative transfer, assuming 1) optical properties can be measured, 2) light propagation is restricted to +x or −x directions, and 3) the tissue light interacts with is homogenous and isotropic. Optical properties under this model include: $\mu_{a1}$=absorption coefficient for 1D geometry, [m$^{-1}$]; $\mu_{s1}$=scattering coefficient for 1D geometry, [m$^{-1}$]; σ=backscattering coefficient where $\mu_{s1}p(+,-)=\mu_{s1}p(-,+)$, [m$^{-1}$]; $p(\hat{x}, \hat{x}')$=scattering phase unction where $\hat{x}$ and $\hat{x}'$ are directional unit vectors; $F_+(x)$=photon flux in +x direction, [Wm$^{-2}$]; $F_-(x)$=photon flux in −x direction, [Wm$^{-2}$]; E=incident (laser) irradiance, [Wm$^{-2}$]. Accordingly, $\mu_{a1}dx$=probability that a photon is absorbed when traversing infinitesimal distance dx; $\mu_{s1}dx$=probability that a photon is scattered into either +x or −x direction when traversing infinitesimal distance dx; $p(\hat{x}, \hat{x}')\mu_{a1}dx$=probability that a photon is scattered from the direction of propagation $\hat{x}'$ into direction $\hat{x}$ when traversing infinitesimal distance dx. The following equations hold true under this one-dimensional transport theory.

1 D transport equations (1) and (2):

$$F_+(x+dx) - F_+(x) = -F_+(x)\mu_{a1}dx - \\ F_+(x)\mu_{s1}dx + F_+(x)p(+,+)\mu_{s1}dx + F_-(x)p(+,-)\mu_{s1}dx \quad (1)$$

$$\frac{dF_+(x)}{x} = -F_+(x)(\mu_{a1} + \mu_{s1}) + F_+(x)\mu_{s1}p(+,+) + F_-(x)\mu_{s1}p(+,-) \quad (2)$$

Backscattering coefficient (3):

$$\sigma = \mu_{s1}p(-,+) = \mu_{s1}p(+,-) \quad (3)$$

Differential photon flux in +x and −x directions, equations (4-1) and (4-2):

$$\frac{dF_+(x)}{dx} = -(\mu_{a1} + \sigma)F_+(x) + \sigma F_-(x) \quad (4\text{-}1)$$

$$-\frac{dF_-(x)}{dx} = -(\mu_{a1} + \sigma)F_-(x) + \sigma F_+(x) \quad (4\text{-}2)$$

1-D fluence equations (5) and (6), where $m = (\mu_{s1}+\sigma)/\sigma_b$ and $b = \sqrt{m^2 - 1}$:

$$F_+(x) = E\frac{m\sinh[b\sigma(D-x)] + b\cosh b\sigma(D-x)]}{m\sinh(b\sigma D) + b\cosh(b\sigma D)} \quad (5)$$

$$F_-(x) = E\frac{\sinh[b\sigma(D-x)]}{m\sinh(b\sigma D) + b\cosh(b\sigma D)} \quad (6)$$

Energy fluence rate can be related to depth or distance by equation (7), where L=radiance, [W/m²*sr]; p=phase of scattering function; S=source of power generated at r in direction of ŝ:

$$\frac{dL(r,\hat{s})}{ds} = -\mu_a L(r,\hat{s}) - \mu_s L(r,\hat{s}) + \mu_s \int_{4\pi} p(s,\hat{s}')L(r,\hat{s}')d\omega' + S(r,\hat{s}') \quad (7)$$

Another function of the invention is to determine the wavelengths of the light before it is emitted and whether different wavelengths of light are emitted simultaneously. Individual (uniband) wavelengths may be emitted, scanning the entirety of the target tissue one wavelength at a time. With time and effort expended up front, this would narrow down the wavelengths that respond to any potential areas of concern. On the other hand, a range or broadband wavelengths may be emitted. Depending on the range of wavelengths, this method would provide a rough analysis in which a larger scope of potential areas of concern would be collected.

We can consider an absorption spectrum of light by an arbitrary mass or volume of tissue. In this case, as the wavelength of light changes, so does the level of absorption by a material. For example, let us assume two arbitrary wavelengths, $\lambda_1$ and $\lambda_2$. At $\lambda_1$, absorption of electromagnetic wave having wavelength $\lambda_2$ can increase and can have some reflection. This could be an effective wavelength to target with a light source because some absorption is desired to distinguish between emitted light and reflected light, which would have a lower relative intensity than that of emitted light. Another wavelength for example at $\lambda_2$, absorption of electromagnetic wave having wavelength $\lambda_2$ may be high. However, it may not produce useful images if most of the light is absorbed and not returned to a detector. Based on absorption spectra of particular materials of interest, such as those of insulin, glucose, hemoglobin, the light sources are configured in a way that emits a range encompassing relevant wavelengths that would produce useful data. In some wavelengths, either lower than $\lambda_1$ and/or longer than $\lambda_2$, the specific material(s) does not have an absorption and is transparent to those wavelengths.

Light sources may be light-emitting diodes, lasers, or broadband sources. LEDs would have a broader wavelength spectrum, but they are less ideal for generating high-resolution, wavelength-specific data. Lasers offer greater precision and specificity of wavelengths, but their power output should be carefully controlled. Specifically, the full width at half maximum of the spectral width of the LED ($\lambda_1$) would generally be greater than that of a laser source ($\lambda_2$). Broadband sources may be better served by LEDs, while uniband sources may be better served by lasers. Alternatively, according to this invention, broadband sources having broader spectrum than the LEDs, can also be used as source 200. Practical configurations of LEDs, broadband sources, and/or lasers as light sources will be apparent to those having ordinary skill in the art.

FIGS. 3A-3E and 3G illustrate arrays of light sources (emitters) in various configurations, in accordance to the present invention, wherein like parts are indicated by like reference numerals as used previously, so that repeated explanation is omitted here. FIG. 3A shows an embodiment wherein an array 400 of light sources has k×n array, representing k numbers of light source in x-direction and n numbers of array in y-direction, where k and n are positive integers. In the embodiment illustrated, each source in array 400, produces light of a certain wavelength; every source in array 400 is a unique source that emits light of relevant wavelengths. For instance, the first source 402 produces light of wavelength $\lambda_1$, an adjacent source 404 produces $\lambda_2$, a source 406 adjacent to that produces $\lambda_3$ and so on. No two sources emit the same wavelength in this configuration. The source emitting light of wavelength $\lambda_{kn}$ 408 is the "knth" source that produces a different wavelength. Alternatively, according to this invention, sources having more than one wavelength can be used in the array arrangement (not shown here).

According to this invention, in some other embodiments, shown in FIG. 3B, sources 402 that emit light having a certain wavelength are grouped together in panels 410. Multiple light sources with the same wavelength are employed to increase the resolution of data acquired from reflected or diffracted inbound light. Each panel 410 produces light waves of a unique wavelength, and the panels 410 are arranged in an array of k panels by n panels. Each panel 410 need not necessarily contain the same number of sources 402. There may be panels that contain a fewer or greater number of sources 402, depending on the characteristics and purpose of a particular wavelength. For example, panel 412 has two sources, and panel 414 has five sources.

Figure 3C:
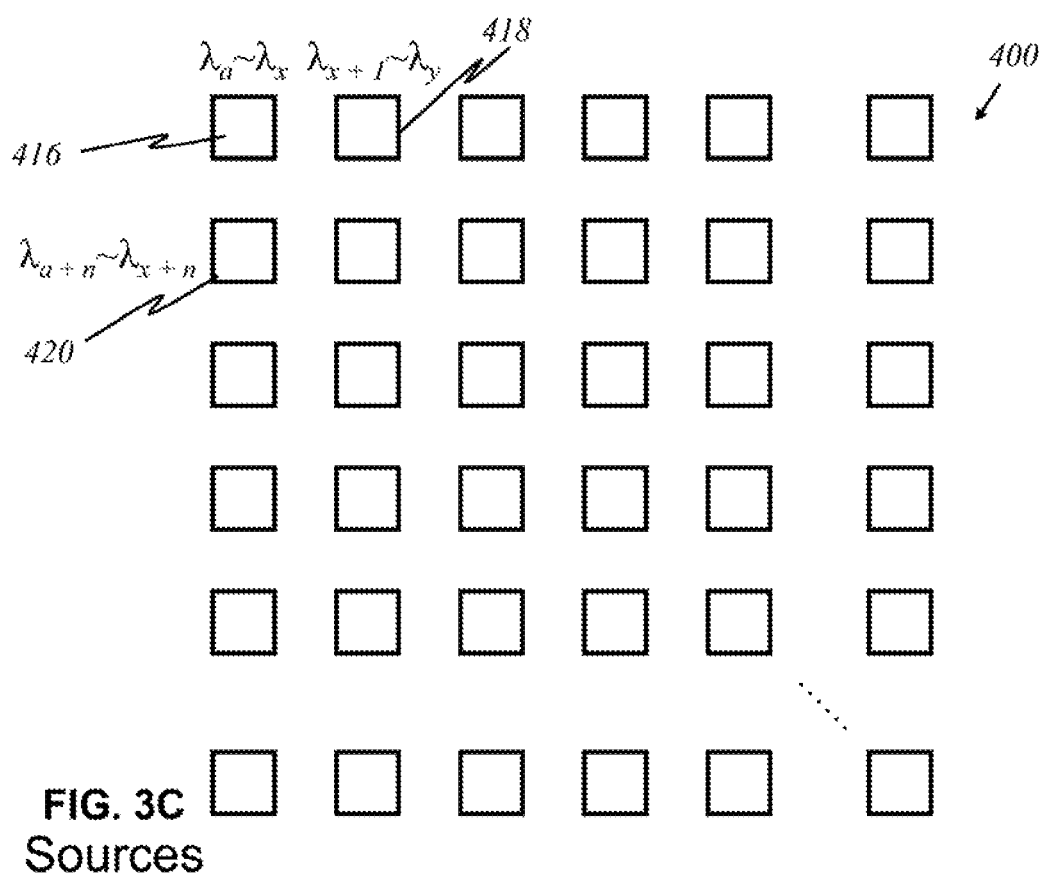

According to this invention, in yet other embodiments, shown in FIG. 3C, alternatively, light sources are broadband sources, which carry multiple signals—that is, emit a range of wavelengths. The ranges of wavelengths of emitted light differ from each other source, and they may overlap. For instance, a source 416 may emit light of wavelengths $\lambda_a$ to $\lambda_x$, where a and x are arbitrary wavelengths. Another source 418 may emit $\lambda_{x+1}$ to $\lambda_y$, where x and y an arbitrary wavelengths, y being greater than x+1. Another source 420 may emit $\lambda_{a+n}$ to $\lambda_{x+n}$, where a+n is between a and x, and x+n is between x+1 and y.

Figure 3E:
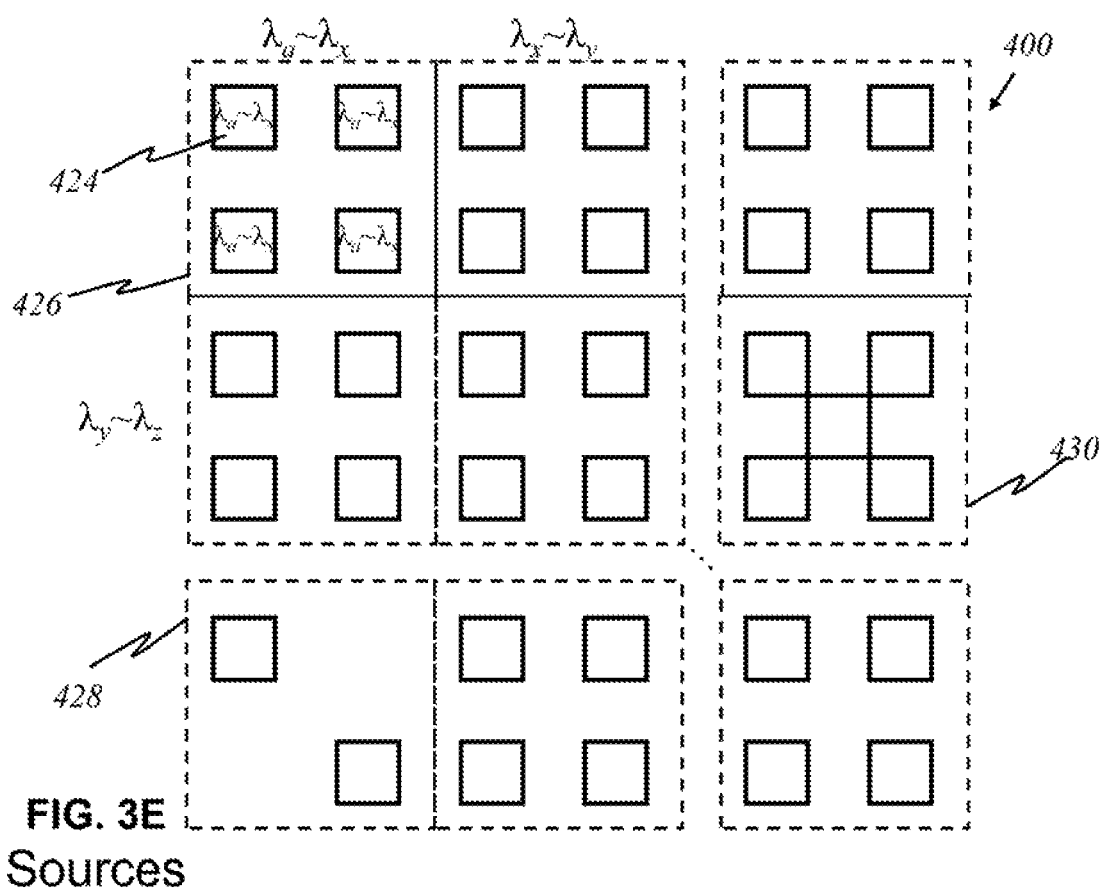

According to this invention, in other embodiments, alternatively shown in FIG. 3D, each source 422 may produce an entire range of desired wavelengths. An array 400 of light sources is shown in FIG. 3I) wherein each source 422 produces light of wavelengths $\lambda_\alpha$ to $\lambda_\Omega$, where $\alpha$ is the smallest relevant wavelength desired, and $\Omega$ is the highest relevant wavelength desired. Such a source 422 may not emit all wavelengths between $\lambda_\alpha$ and $\lambda_\Omega$, only the relevant ones within that range. Broadband sources 424 may be grouped into panels 426, as shown in FIG. 3E. Similar to the arrangement in FIG. 3B, each panel 426 has sources 424 emitting light of the same range of wavelengths. The number of sources 424 may differ for each panel. There may be panels 428, 430 that contain a fewer or greater number of sources, depending on the characteristics and purpose of a range of particular wavelengths.

Figure 3G:
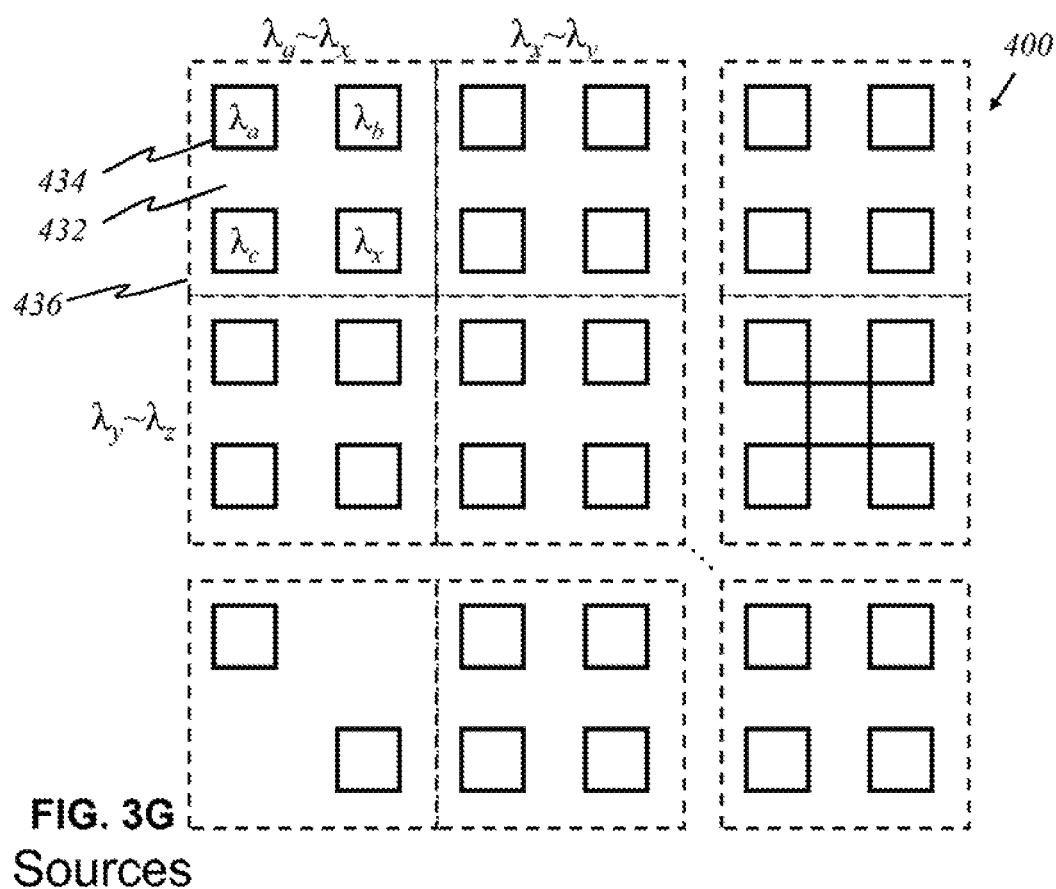

FIG. 3F is an illustration of a light source with a filter 432 that allows certain wavelengths to pass through while blocking other wavelengths in the preferred embodiment, according to this invention, wherein like parts are indicated by like reference numerals as used previously, so that repeated explanation is omitted here. Here, a broadband source 434 generating light 436 of multiple wavelengths $\lambda_1$ through $\lambda_5$ exits through filter 432. Filter 432 has openings that permit light of wavelengths $\lambda_1, \lambda_2, \lambda_3, \lambda_4$, and $\lambda_5$ to pass through. The result is effectively five light sources that each emits light that is no longer the original light generated by the broadband source. Its utility is illustrated in FIG. 3G, where light sources 434 are grouped together in panels. The number of sources may differ for each panel. There may be panels that contain a fewer or greater number of sources. Each panel comprises an underlying broadband source that produces light waves of multiple wavelengths. For example, underneath upper-left panel 436 is a broadband source that emits light of wavelengths $\lambda_x$ through $\lambda_x$, of which four distinct wavelengths $\lambda_a, \lambda_b, \lambda_c$, and $\lambda_x$ are relevant and of interest. By placing filter 432 over the source panel, one source is simply divided into multiple light sources that effectively function like the individual sources in FIG. 3A.

FIG. 4A illustrates the major components of a light detector 500 that registers light of particular wavelength(s) in a preferred embodiment, according to this invention, wherein like parts are indicated by like reference numerals as used previously, so that repeated explanation is omitted here. Each base detector component 502 is identical in that it detects the presence of light. To detect light of a particular wavelength or wavelengths, a filter 504 installed over the detector varies among each detector 500. Filter 504 blocks out other wavelengths, letting only particular wavelength(s) through. For example, if filter 504 is designed to allow only waves having wavelengths $\lambda_1$ and $\lambda_3$, light having other wavelengths, such as $\lambda_2$, are blocked. Thus, depending on the function of the filter, detector 500 becomes able to detect only desired wavelengths.

FIG. 4B shows a preferred embodiment of an array 506 of such detectors, the array having width k and length n, in accordance to this invention, wherein like parts are indicated by like reference numerals as used previously, so that repeated explanation is omitted here. Each detector 508 can only see and detect the presence of light of a certain wavelength: $\lambda_1, \lambda_2, \lambda_3$, etc. A detector that detects light of wavelength $\lambda_{kn}$ 510 is the "knth" detector that registers that wavelength. If light of a particular wavelength $\lambda_x$ reaches array 506 of detectors, only one detector will recognize it.

Figure 4C:
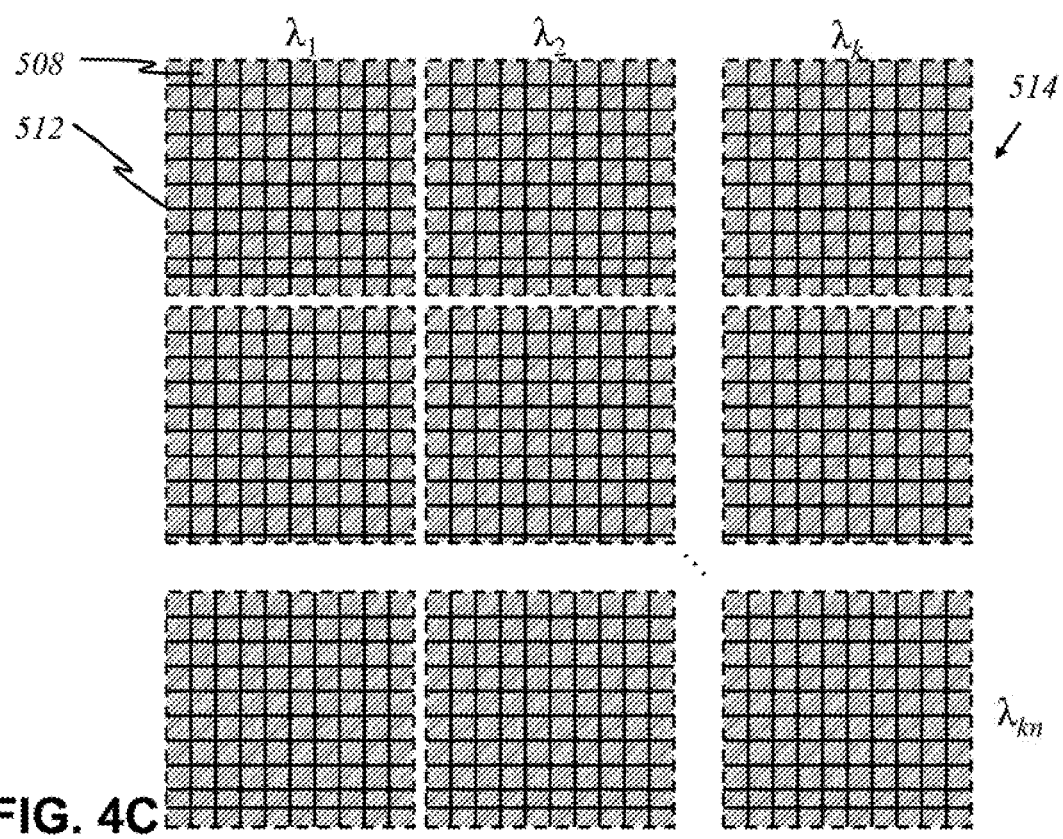

In another preferred embodiment according to this invention, alternatively, detectors 508 that see light of a certain wavelength are grouped together in panels 512, shown in FIG. 4C. Multiple detectors 508 are employed to detect the same wavelength increases the resolution of data acquired by reflected or diffracted light. Each panel 512 detects light of a particular wavelength, and the panels are arranged in an array 514 of k panels by n panels. In some embodiments, however, a filter is unnecessary for a base detector component to detect a particular wavelength; such a detector inherently has the capability to detect a unique wavelength or a narrow range of wavelengths.

Figure 5B:
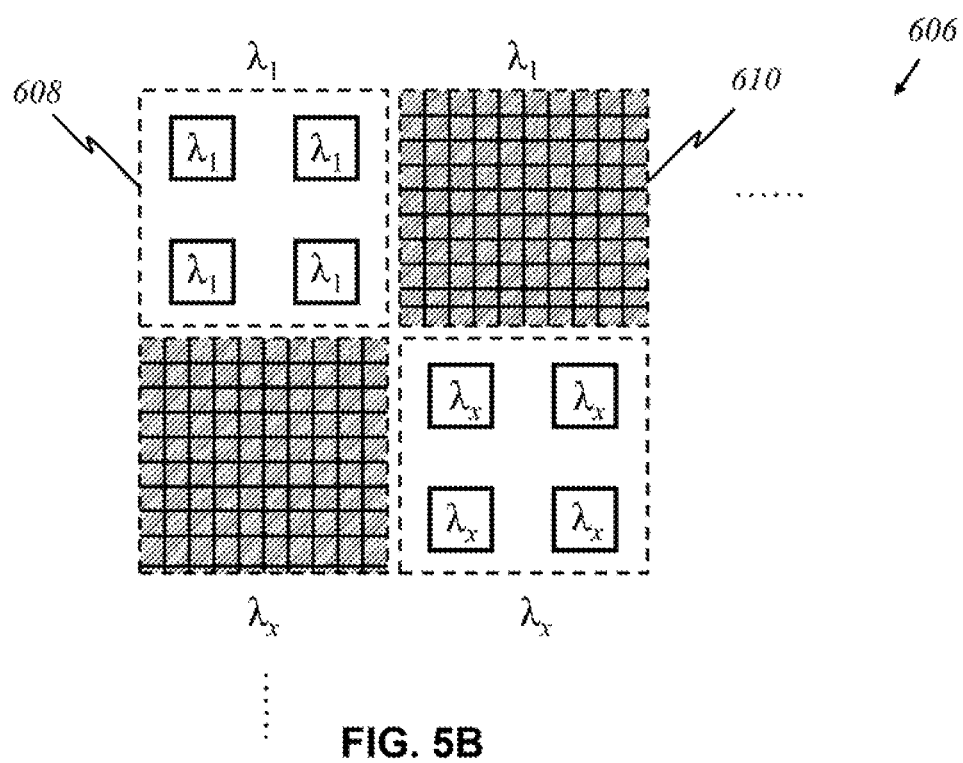

In yet other embodiments, rather than arranging light sources and detectors separately from each other, the sources and detectors can be placed together, as shown in FIGS. 5A-5E. In FIG. 5A, sources 600 that emit light of a certain wavelength and detectors 602 that detect light of a certain wavelength alternate on a source-detector array 604 of width 2k and length 2n.

According to this invention, in another preferred embodiment shown in FIG. 5B, panels of multiple sources and detectors, rather than individuals, alternate in a source-detector-panel array 606. A panel comprising sources 608 emitting light of wavelength $\lambda_1$ is adjacent to a panel of detectors 610 that detect only $\lambda_1$. Other panels emitting and detecting light of arbitrary wavelength $\lambda_x$ are arranged similarly.

In another preferred embodiment shown in FIG. 5C, broadband sources and specific detectors are placed in alternating fashion on an array 612 of width 2k and length 2n. Similar to the arrays illustrated in FIGS. 3C-3E, broadband source 614 here may be capable of emitting a narrow range, a wide range, or any range of relevant wavelengths. Each detector 616 or group thereof, however, registers a particular wavelength. One having ordinary skill in the art is able to create further variations in arrangements of light sources and detectors.

Figure 5E:
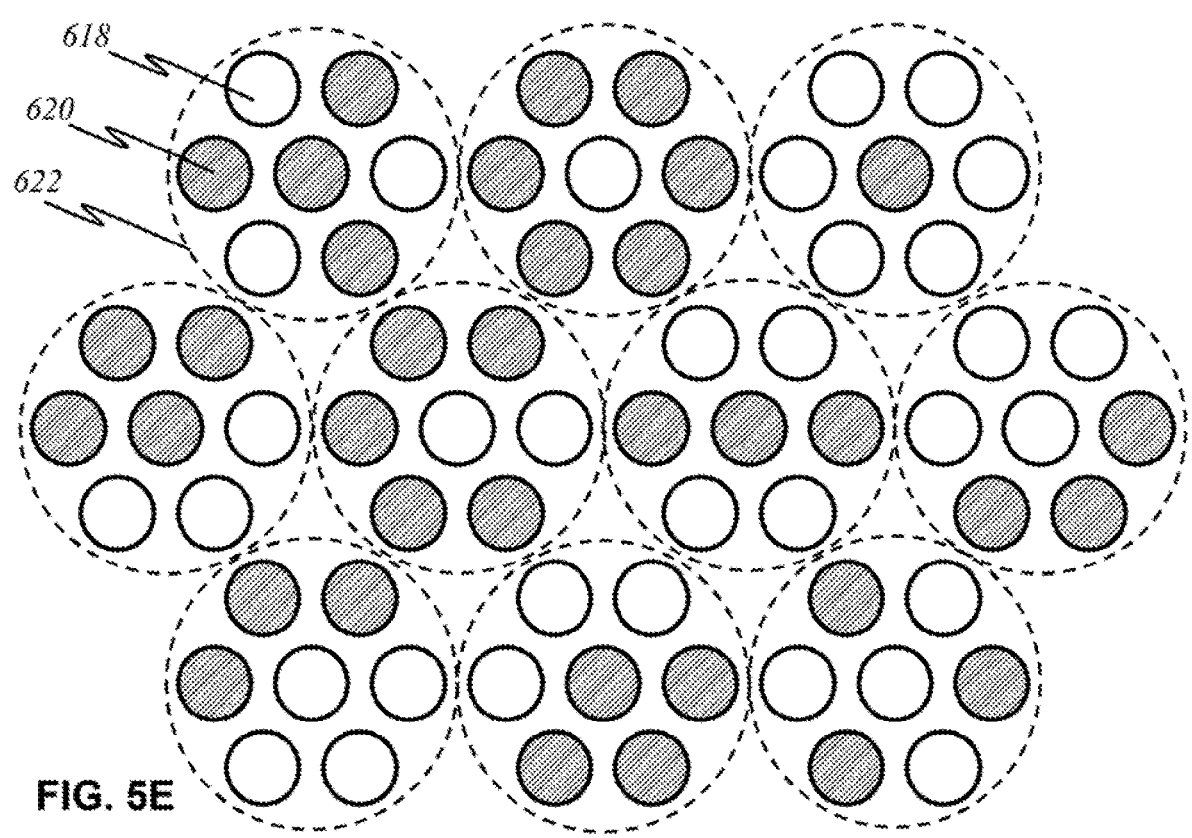

Other arrangements are possible in other embodiments. For instance, FIG. 5D illustrates sources 618 and detectors 620 of circular shape positioned in a space-efficient manner. FIG. 5E illustrates circular sources 618 and circular detectors 620 grouped in various combinations within panels 622. Similar to the previously described embodiments, sources 618 may be capable of emitting a narrow range, a wide range, or a range of relevant wavelengths. Each detector 620 or group thereof detects a particular wavelength. Other possible arrangements, shapes, and configurations (not shown here) will be apparent based on the aforementioned disclosures.

The various arrangements of the elements of the present invention manifested in a device will now be described in further detail. To emit light and detect reflected or diffracted light, light sources and detectors must be arranged in a way to emit appropriate wavelengths of light toward the user's tissue and detect light that returns from the user's tissue. The device can take numerous forms to provide such functions. In some embodiments, one general shape of the device could be a hemisphere with a hollow interior cavity. In other embodiments, it could be a curved surface for making direct contact with the tissue. In yet other embodiments, it could be a more compact device that can flip open and engage panels of sources and detectors. Other arrangements, features, structural dimensions, shapes, materials used, etc., allowing detectors to receive light reflected or diffracted from the tissue will be apparent to those having ordinary skill in the art.

Figure 6:
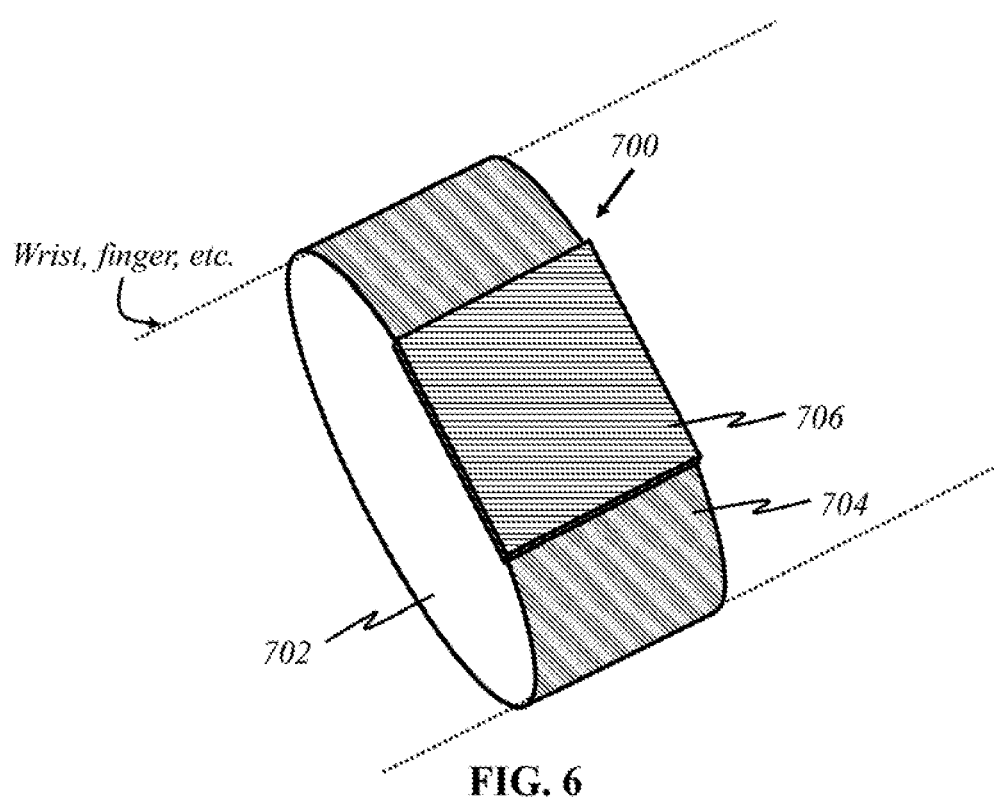
FIG. 6 shows an angled view of a preferred generic wearable device according to the present invention.

FIG. 6 shows an angled view of a wearable device 700 that detects components of interest, such as ions and molecules, in bodily fluids, such as sweat and respiratory fluids. This wearable device may use the electronic circuit of FIG.

1 to detect trace amounts of ions. This wearable device may also use optical components of FIGS. 2-5 to detect concentration of glucose in the blood. In a preferred embodiment, device 700 is wearable on a user's wrist through an opening 702 created by wrapping a fastening apparatus, such as a strap 704, similar to a wristwatch. Device 700 may be wearable in other ways, such as making strap 704 rigid, smaller than a wristwatch, and in a fixed position, similar to a ring. Thus, wearable device 700 may be used with any elongated appendage, such as a finger or wrist. Both embodiments are amenable to being worn at substantially all times of the day, allowing constant monitoring of the user's metabolites (e.g., glucose levels, molecular concentration in blood, ionic concentration in blood). The presence of certain molecules present in bodily fluids is an indicator of diabetes, which the present invention uses as a factor in increasing the confidence of the existence of diabetic symptoms. A panel 706 is mounted on strap 704. Panel 706 contains micro- and nanoscaled components, such as the circuit of FIG. 1 and components of FIG. 2, among others, that operate together to allow detection of components of interest. Panel 706 may contain optical components as described in text accompanying FIGS. 2-5.

Figures 7A, 7B:
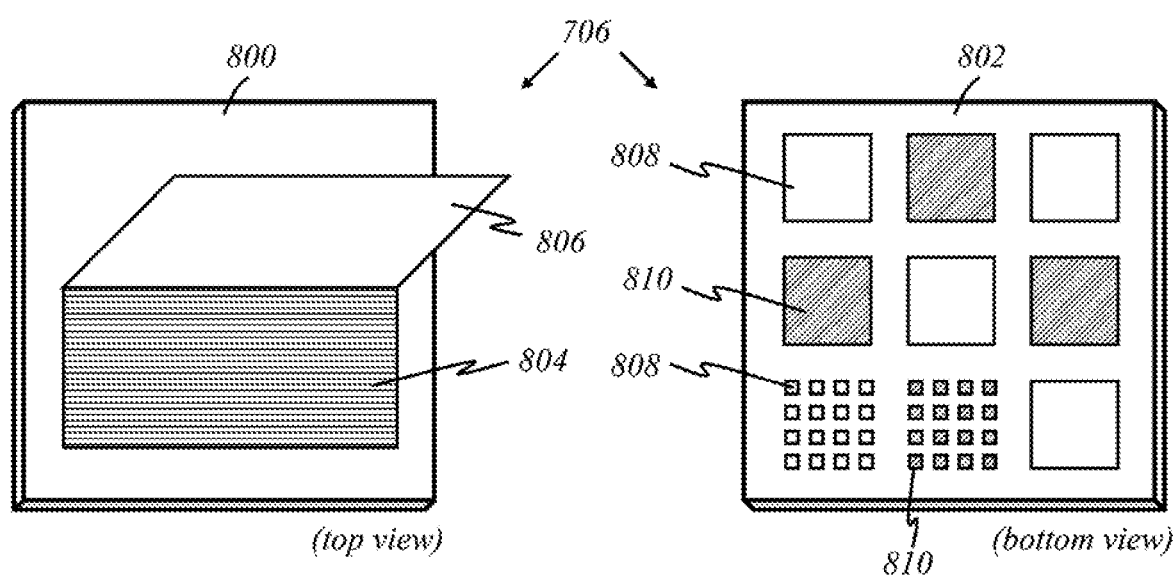

FIGS. 7A through 7D show schematics of a preferred embodiment of a front side 800 and a back side 802 of panel 706, wherein like parts are indicated by like reference numerals as used previously, so that repeated explanation is omitted here. In FIG. 7A, a nano-membrane 804 (see nano-membrane 114 of FIG. 1) is showing on the surface of front side 800. Nano-membrane 804 allows very small particles, such as $H^+$ or $CO_2$ ions, to pass, but not larger macromolecules such as proteins. In some embodiments, the pores may be large enough for glucose molecules to enter. Nano-membrane 804 is easily accessible for a user to breathe on (expelling respiratory fluids directly onto nano-membrane 804), apply sweat, lick, or otherwise provide a nominal amount of bodily fluid. When not in operation, a cover 806 may shield nano-membrane 804 from excessive exposure to undesirable elements, such as air, dust, or other fluids that are present in everyday life. Front side 800 may have other mechanisms for controlling wearable 700 device, not shown in this illustration.

FIG. 7B is a schematic of panel 706 that utilizes optics. Light sources 808 and light detectors 810, or panels 808, 810 thereof, are embedded on back side 802 of panel 706. Sources 808 and detectors 810 may be arranged in many ways and in many sizes; the shown arrangement is an exemplar. This optical setup faces the user's skin. Sources 808 emit light of varying wavelength and intensity to penetrate the skin. Detectors 810 receive returning light. Optical signals received are converted to electrical signals for processing or routed first through optical-fiber cables and/or a lens to a processor (not shown here) before being converted to electrical signals.

Wavelengths of returning light vary based on the material from which the light is coming. For example, if light has penetrated through to a blood vessel and is returning after reflecting, refracting, or diffracting from blood, other electronic or logical components within panel 706 can recognize the material as blood based on comparison with known data. Once blood is recognized, the composition and concentration of present components in the blood may also be recognized by analyzing wavelength and absorption spectra. The concentration of glucose present in blood is an indicator of diabetes, which the present invention uses as a factor in increasing the confidence of the existence of diabetic symptoms.

In FIG. 7C, a schematic of another electronic example of back side 802 of panel 706 is shown, wherein like parts are indicated by like reference numerals as used previously, so that repeated explanation is omitted here. Nano-membrane 804 is placed for capturing fluids and components of interest therein from the user's skin facing back side 802. Functions include those described above for FIG. 7A. This positioning is beneficial for regular monitoring of bodily fluids because nano-membrane 804 is exposed to skin, which produces sweat.

In FIG. 7D, a rough surface 808 acting as an interface for an electronic circuit is showing on the surface of back side 802. Rough surface 808 feels soft to the touch but has a defined pattern on a miniscule scale. Rough surface 808 assists in collection of fluids and components of interest therein. In the micro- or nanoscale, rough surface 808 comprises bumps (not shown here, see FIGS. 7E and 7F) that serve to slow down the flow of fluids across the surface. Nanopores exist between the bumps, the nanopores allowing fluids to enter along with components of interest. Pores lead to the depletion layer (not shown here, see FIG. 1A). When not in operation, a sliding cover 810 may shield rough surface from excessive exposure to undesirable elements, such as air, dust, or other fluids that are present in everyday life. Sliding cover 810 may be used with every embodiment disclosed in FIGS. 7A-7C, and vice versa. Sliding cover 810 is an example of a means to cover sensitive parts of the wearable device.

Figure 7E:
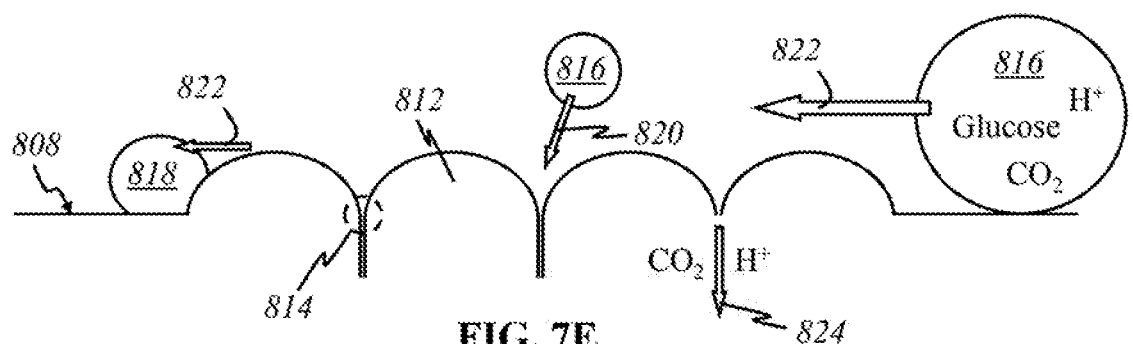
FIGS. 7E and 7F show cross-sectional, close-up views of bumps, components of the embodiment of FIG. 7D.

A close-up schematic of rough surface 808 is shown in FIG. 7E in a cross-sectional view. Numerous bumps 812 are lined up across rough surface 808. Bumps 812 are spaced apart such that there is space for an opening 814 in between. As droplet of fluid 816 acquired from the body via—e.g., evaporation of sweat from skin, application of saliva, expulsion of breath—contacts rough surface 818, approaches bumps 812, and starts to roll over bumps 812, droplet 816 deteriorates because bumps 812 intercept and break up droplet 816 as it rolls over them, resulting in small droplet 818, if any.

A first representative route 820, a second representative route 822, and a third representative route 824 indicating possible paths of movement of droplet 816 are shown in FIG. 7E. Portions of droplet 816 move through pores 814 by various ways, e.g., gravity, centrifugal force on the device, or capillary action. Droplet 816 may reach pores 814 by evaporation along representative route 820. It may also roll across route 822. Pores 814 lead to the depletion layer (not shown here, see FIG. 1A) via representative route 824, which affects the resistance of the depletion layer and allows the circuit in panel 706 to determine the concentration of components of interest that exist in droplets 816 as described in the text accompanying FIGS. 1A-1C.

Figure 7F:
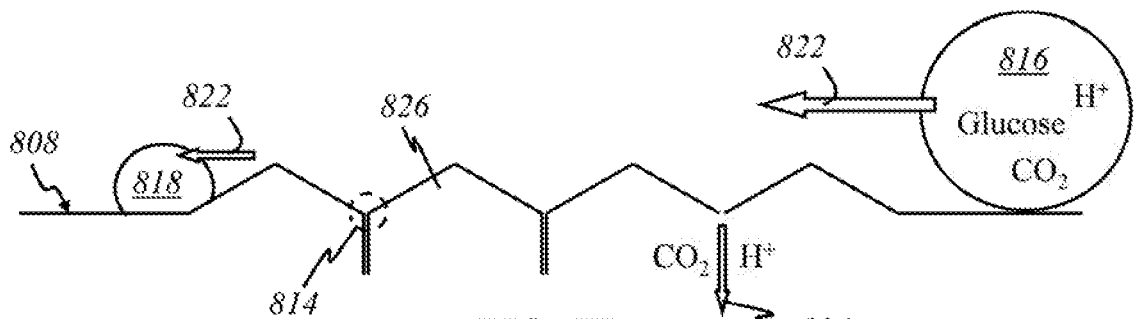

FIG. 7F shows rough surface 808 similar to that of FIG. 7E, wherein like parts are indicated by like reference numerals as used previously, so that repeated explanation is omitted here. The main difference is that bumps 826 are not rounded like bumps 812 of FIG. 7E but jagged. Various shapes and combinations of shapes will be apparent to those having ordinary skill in the art.

Figure 8A:
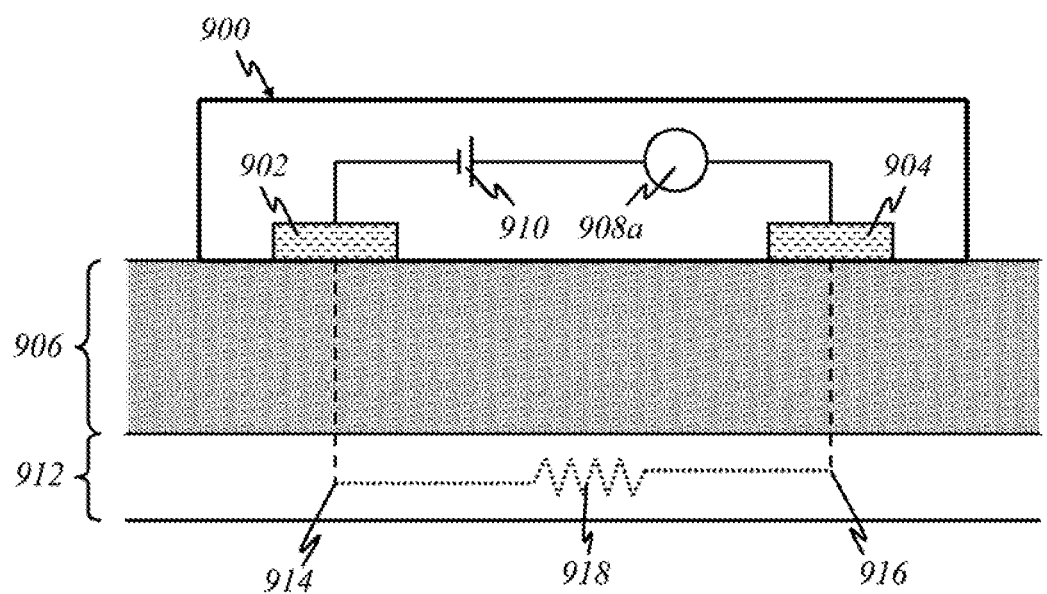
FIGS. 8A-8C show cross-sectional views of a device that detects metabolites using induced resistivity according to the present invention.

FIG. 8A shows a cross-sectional schematic of a device 900 that detects components of interest, such as glucose and other molecules generally too large for motility through nano-channels, using induced resistivity ("resistivity embodiment"). Device 900 may be part of a wearable device similar to that of FIG. 6. It may be on a separate module, such as a handheld device. Device 900 is comprised of a first metallic plate 902 and a second metallic plat 904 separated by a distance. Device 900 is operable by being placed above an area of skin 906. A current 908a flows through a wire, driven by a battery 910. A biological structure carrying bodily fluids (e.g., lymphatic vessel, capillary, artery, vein) or, shown as an exemplar, a blood vessel 912 under skin 906 is affected by the current generated by device 900. Between a first point 914 directly under first plat 902 and a second point 916 directly under second plat 904, a resistance 918 (and by extension, a conductance) is created. This resistance is variable based on the concentration of glucose in the blood. By measuring resistance 918 across points 914, 916, concentration of glucose can be derived.

Figure 8B:
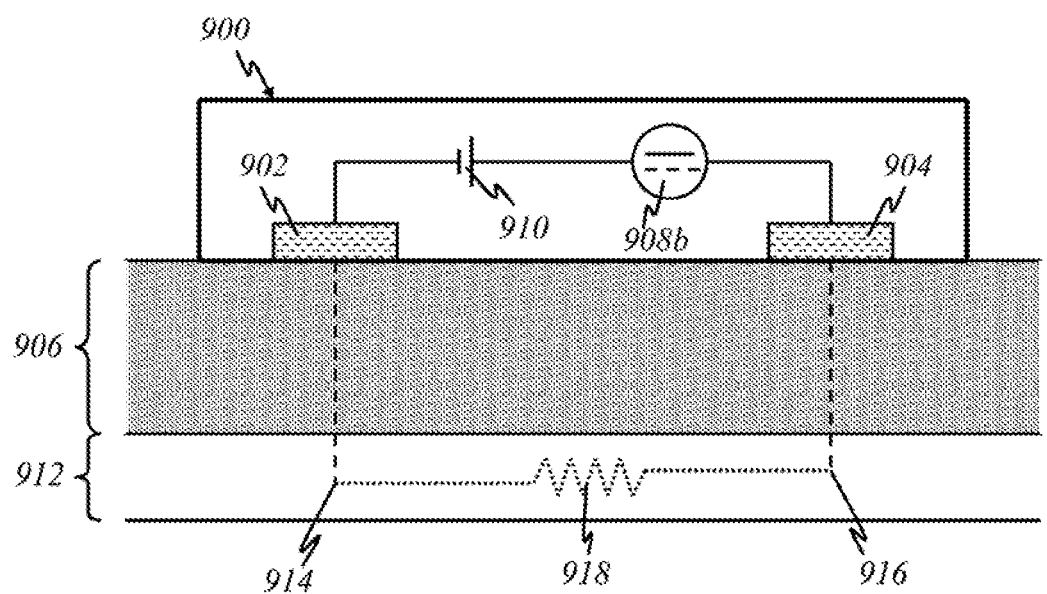
Figure 8C:
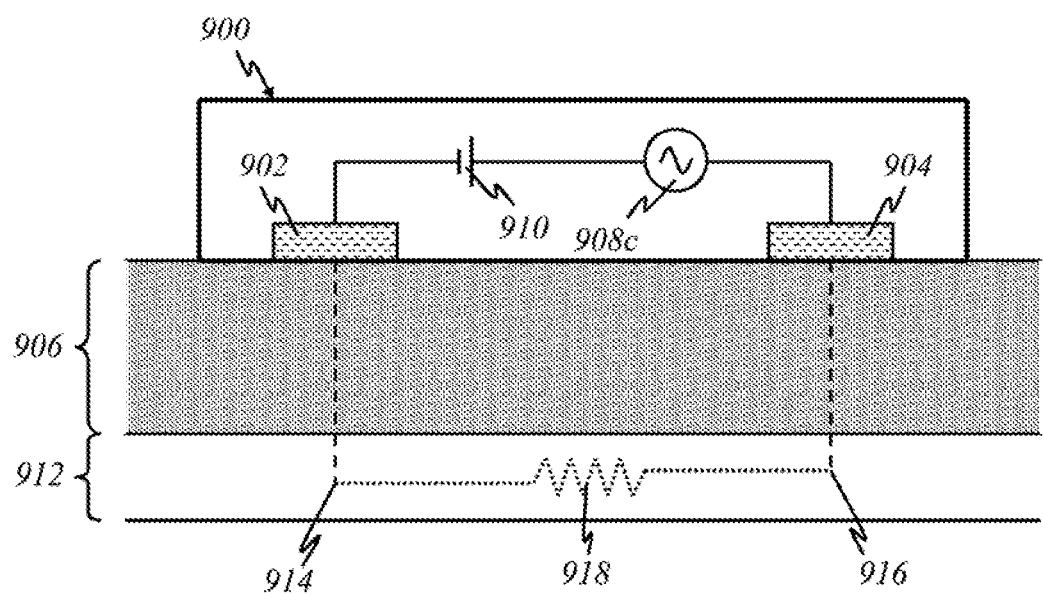

FIG. 8B shows a cross-sectional schematic of device 900, which detects components of interest. It is a specific embodiment of that shown in FIG. 8A, wherein like parts are indicated by like reference numerals as used previously, so that repeated explanation is omitted here, wherein the current through the wire is a direct current (DC) 908b. FIG. 8C is another specific embodiment of that shown in FIG. 8A, wherein the current through the wire is an alternating current (AC) 908c.

FIG. 8D shows a frontal view of the interface of device 900, which makes contact with the user's skin. Metallic plats 902, 904 are shown facing outward from device 900. FIG. 8E shows an angled view of the same device. There may be a cable 920a that connects to a separate mainframe apparatus (not shown here) that performs calculations.

Figure 9A:
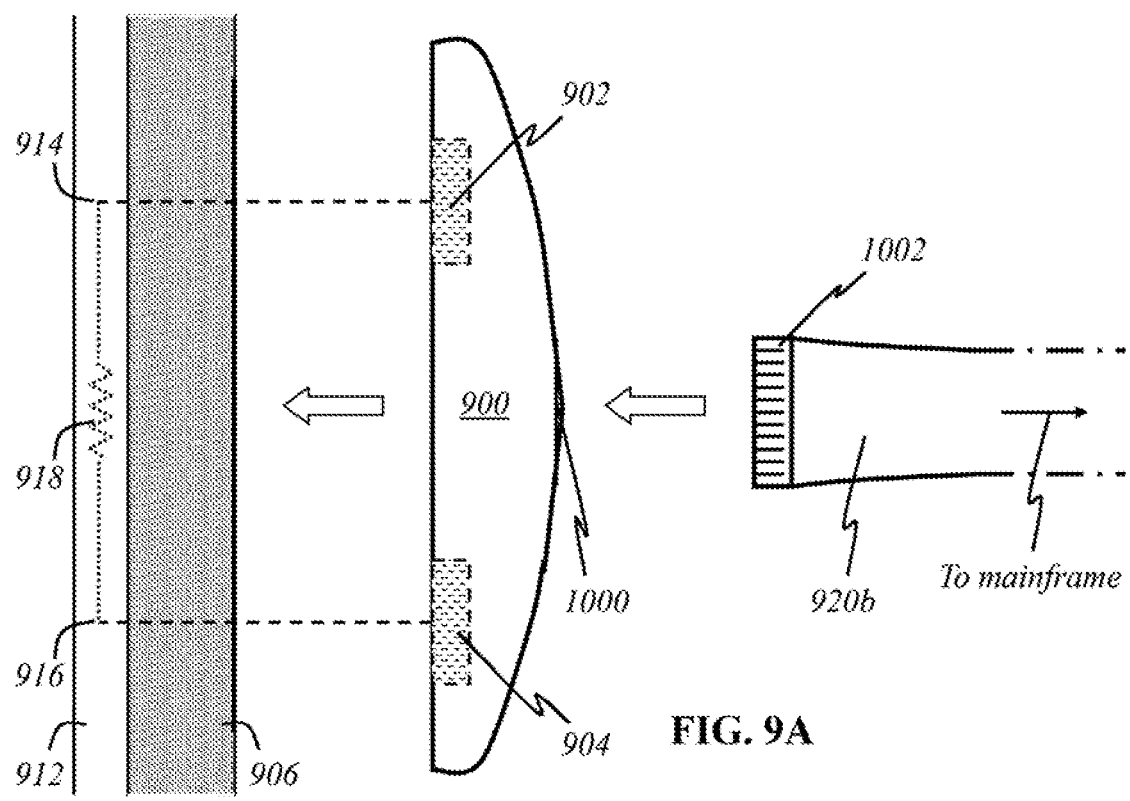
FIG. 9A shows a cross-sectional view of the device of FIGS. 8A-8E and a cable that may connect to the device.

FIG. 9A is a schematic showing a cross-sectional view of a preferred embodiment for a resistivity embodiment, taken along A-A' direction of FIGS. 8D and 8E, according to this invention, wherein like parts are indicated by like reference numerals as used previously, so that repeated explanation is omitted here. Device 900 is shown approaching skin 906 and blood vessel 912. Once the surface of device 900 having metal plats 902, 904 makes contact with skin 906, resistance 918 is created between points 914, 916. Furthermore, in this embodiment, device 900 is disconnected from the mainframe apparatus (not shown here) that performs calculations. A detachable electric ribbon cable 920b is shown approaching the back side of device 900, wherein a socket 1000 is present for connection between device 900 and cable 920b. A connector 1002 on cable 920b provides a means for connecting with socket 1000. In some embodiments, device 900 can be connected to the mainframe by inserting connector 1002 of cable 920b into socket 1000 present on the outer shell of the device. Having electrical cable 920b and detaching it from device 900 into separate components is possible and useful for compact storage. Cable 920b is preferably a ribbon cable, whose flat and flexible characteristics make it compact and simple to store or transport.

Figure 9B:
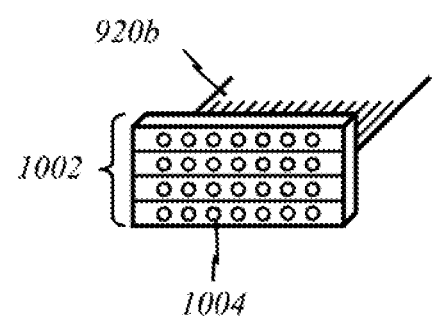
FIG. 9B shows separately a connector, a component of the cable shown in FIG. 9A.

Instead of a flat interface, larger electric pins 816 or other means of making contact with circuitry components may also be used. FIG. 9B is a schematic showing an enlarged view of the front of connector 1002 of cable 920b, which allows connection to socket 1000 via electric pins 816 as a connection interface alternate to that of the ribbon cable. Socket 1000 would have a shape that differs from that for a flat interface, according to the shape shown in FIG. 9B.

Figure 10A:
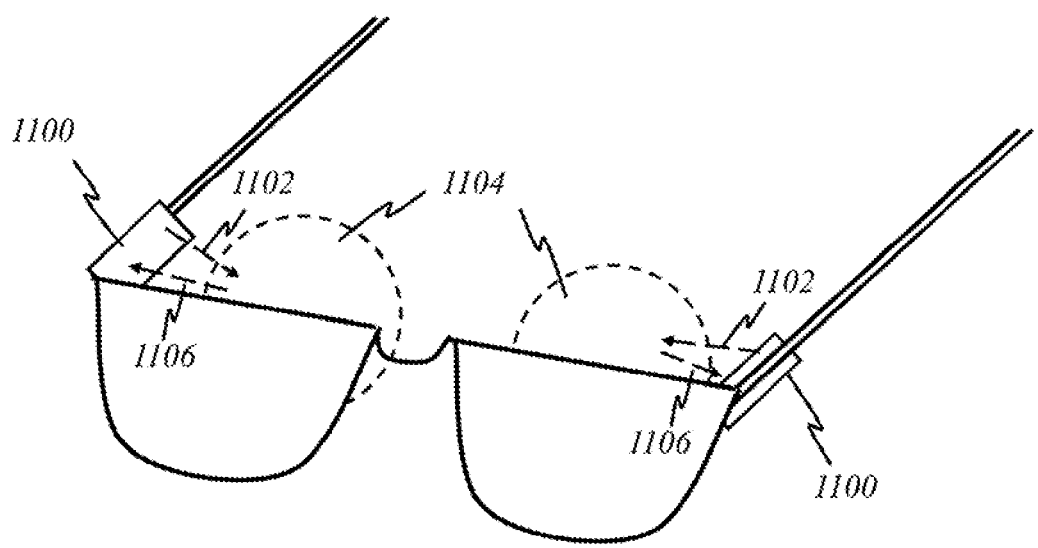
FIG. 10A shows a wearable device that detects metabolites optically according to the present invention, implemented in eyeglasses.

FIG. 10A is a schematic of a preferred embodiment of another wearable device, wherein a panel 1100 of light sources and light detectors, or collections thereof, are fixed on each arm of wearable eyeglasses. Each arm act as a fastening apparatus to hold the eyeglasses in substantially the same position on the user's ears and face. Panel 1100 emits incident light 1102 toward an eyeball 1104 of the wearer of the device. Light 1102 diffracts, reflects, or fluoresces from within the vitreous humor of eyeball 1104 before coming back as a returning light 1106.

These optical setups face toward the user's eyes. Sources 1108 emit light of varying wavelength and intensity to penetrate the skin, bones, and surface of eyeball 1104. Detectors 1110 receive returning light. Wavelengths of returning light vary based on the material from which the light is coming. For example, if light has penetrated through to the vitreous humor of eyeball 1104 and is returning after reflecting, refracting, or diffracting from the vitreous humor, other electronic or logical components within panel 1100 can recognize the material as blood based on comparison with known data. Once vitreous humor is recognized, the composition and concentration of present components, glucose in particular, may also be recognized by analyzing wavelength and absorption spectra. The concentration of glucose present in the vitreous humor is an indicator of diabetes, which the present invention uses as a factor in increasing the confidence of the existence of diabetic symptoms.

Figure 10B:
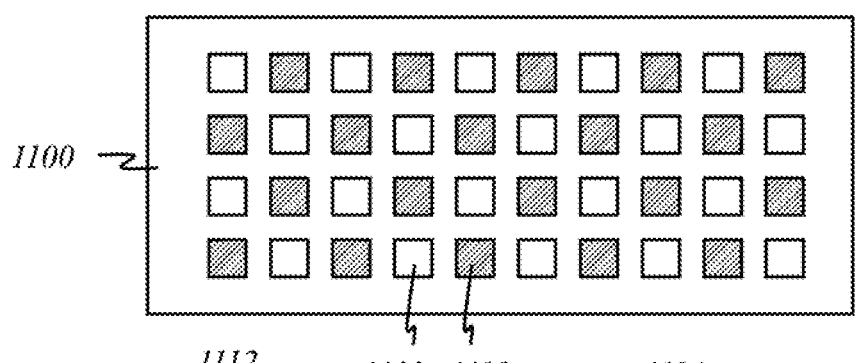
FIGS. 10B and 10C show examples of light source and detector arrangements in panels, components of the wearable device of FIG. 10A.
Figure 10C:
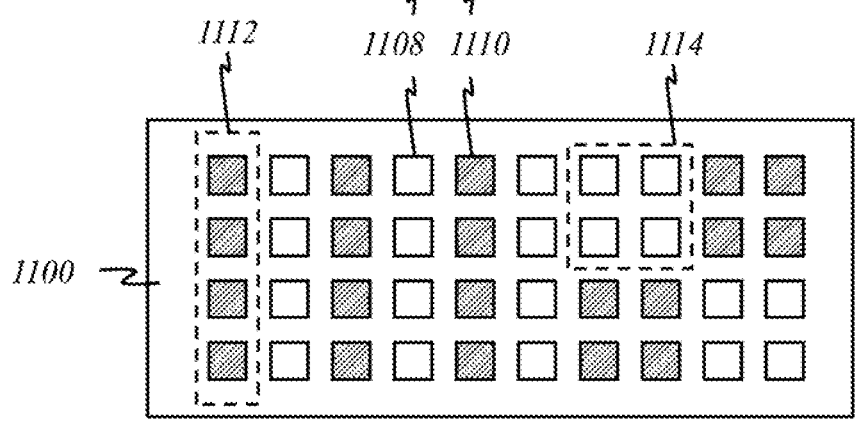

FIGS. 10B and 10C show schematics of arrangements of light sources 1108 and light detectors 1110 on panel 1100. Sources 1108 and detectors 1110 may be arranged in many ways; the shown arrangements are exemplars. Sources 1108 and detector 1110 may have one pattern of alternation, as in FIG. 10B. They may be grouped into collections, as in FIG. 10C. A panel or a collection 1112 is a group of detectors 1110. A panel or a collection 1114 is a group of sources 1108.

FIG. 11A shows a cross-sectional, top view of an alternate preferred non-contact embodiment of the device, which has pane 1200 suspended over a surface of a section of skin tissue 1204 ("non-contact embodiment"). Side panes 1202 may have soft support pad 1203 that allows the device to rest on patch of skin 1204 and maintain a constant distance with pane 1200. According to this invention, to make the device compact, the device comprises at least one foldable pane amenable to handheld use and transportation. Alternatively, the device can have more than one pane, wherein each pane 1200 holds light sources 1212 and detectors 1214, or panels thereof (see FIGS. 11B and 11C). In this embodiment, center pane 1200 holds light sources and detectors facing section of skin tissue 1204. Hinges 1206 allow side panes 1202 on the side to rotate along arcs 1208 and be held at desired angles relative to center pane 1200. There may be a handle 1210 or other means to grasp the device during operation.

FIG. 11B is a schematic showing a front view of the preferred embodiment for non-contact device according to this invention, wherein like parts are indicated by like reference numerals as shown in FIG. 11A, so that repeated explanation is omitted here. In FIG. 11B, side panes 1202 have been unfolded and are facing outward. Sources 1212 and detectors 1214 are individually placed on center pane 1200, although they may be grouped together in panels and may be broadband or uniband sources (see FIGS. 3-5). Alternatively, other variations of placement of sources 1212 and detectors 1214 are possible, for example, as illustrated in FIG. 11C. Here, the main difference from FIG. 11B is that sources 1212 and detectors 1214 are grouped in panels on center pane 1200.

During operation of the non-contact embodiment, the user places the device with pane 1200 and side panes 1202 opened on top of an area of skin with visible defect, such as the forearm with a colored spot—an area of interest. The user may require manual operation to receive sufficient data to image the epidermal and dermal layers of the skin along with any areas of interest. For instance, the user may need to slowly move the handheld device across the skin over sufficient amount of distance and area of the skin to scan it. Unlike some other preferred embodiments previously disclosed, there is no need to press the device into surface of skin 1204. In the embodiment illustrated in FIGS. 11A-11C, while the device is in operation, broadband or uniband light sources 1212 from center pane 1200 emit light 1220 of varying wavelengths toward the object, i.e., skin, placed between side panes 1202. Reflected, diffracted, or fluoresced light 1222 travels back to a detector or panel thereof, on side panel 1202. If the detector is able to detect the particular wavelength of the light wave, it then processes the signal for imaging or sends it to the mainframe (not shown) via optical, electrical, or wireless connection for further processing and imaging. Based on known values of wavelengths that would be returned after reflecting or diffracting from skin cancer tumors rather than known values of wavelengths that would be returned after reflecting off healthy skin tissue, the processor can determine the position and depth of the returning light to locate potential cancerous lesions. Three-dimensional images are also produced from all returning light waves; thus, potentially cancerous lesions can be viewed and interpreted with human eyes.

Figure 12A:
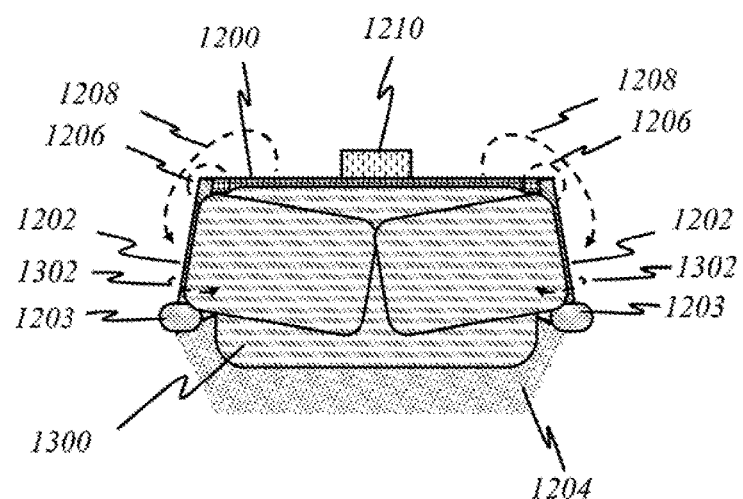
FIG. 12A shows a schematic of another "non-contact" embodiment in a top view.

One way to protect the user from overexposure to light is to place shields between the user's line of sight and light sources. FIG. 12A is a schematic showing a top view of the preferred embodiment for an alternate device, according to this invention, wherein like parts are indicated by like reference numerals so that related explanation is omitted here. The main difference from FIG. 11A is that shields 1300 are placed over panes 1200, 1202. Shields 1300 are deployed by unfolding them upward from panes 1200, 1202 along arcs 1302. They are composed of any material that will not be penetrated by the light wavelengths that are used by the device. Such a material should absorb rather than reflect. Alternatively, shields 1300 can be made from materials that can prevent light from partially or wholly escaping outside, such as a polymer, plastic, nano-composite fiber, carbon fiber, etc. Similar to panes 1200, 1202, shields 1300 can be adjusted and held at desired angles. In the illustration, engaged shields 1300 are locked into a substantially perpendicular angle with respect to panes 1200, 1202. The enclosure created by panes 1200, 1202 and shields 1300 minimizes the leakage of light 1220, 1222 from light sources 1212. In turn, the user is less likely to be irritated by light that she may see or wavelengths that may be harmful to the eyes during operation. The shield can be made from the material the type of which can be selected from the group consisting of polymer, plastic, nano-composite having the capability of absorbing the light having wavelengths to be absorbed. Alternatively, the shield can be made from the material which could be reflective for the light wavelengths of interest. In this case, the secondary reflective light from the shield are made to incident onto the detector(s) array (not shown here) for further processing the signal. The signal can be synchronized or asynchronized with the main detector panel described earlier. In this case, the shields can be designed in such a way that incoming lights and outgoing light (reflective) can be same direction or different direction (not shown here).

FIG. 12B is a schematic showing the device with front shield 1300, as shown in FIG. 11A, according to this invention, wherein like parts are indicated by like reference numerals so that related explanation is omitted here. In FIG. 12B, side panes 1202 have been unfolded and are facing outward. Sources 1212 and detectors 1214 are individually placed on center pane 1200, although they may be grouped together in panels 1304 and may be broadband or uniband sources as shown in FIGS. 3-5). Shields 1300 prevent light emitted by the sources from reaching the user's line of sight which remains above shields 1300 during normal operation. FIG. 12C is a schematic showing the same embodiment. The main difference from FIG. 12B is that sources 1212 and detectors 1214 are grouped in panels on center pane 1200. From the aforementioned disclosures, other useful configurations will be apparent to those having ordinary skill in the art.

FIG. 13 is a schematic showing a close-up view of an optical-fiber cable 1400, which comprises a bundle of optical fibers 1402. Numerous optical fibers 1402 are packed into cable 1400. Optical fibers 1402 are transparent and highly flexible fibers that are typically at most 0.5 mm. They can function as a waveguide for light 1404 traversing through. Containment of light 1404 is enabled by total internal reflection, which completely reflects light propagating along fiber 1402 hits the boundary of fiber 1402 at a critical angle, ideally close to parallel with the walls of fiber 1402. To confine and propagate light 1404 within fiber 1402, the light that enters cable 1400 must be within a certain range of angles, which a lens may assist with.

FIG. 14 is a schematic showing a whole view of implementations of operational parts of the preferred embodiment, according to this invention. A user end 1500 is the handheld portion for the user to aim and receive light. In embodiments using optical fibers to transfer light signals, light 1502 may be generated by sources placed in a mainframe 1504 rather than user end 1500. Likewise, detectors may be placed in mainframe 1504 rather than user end 1500. In other embodiments, sources and detectors may be placed on user end 1500, with a generic connection 1506a transferring data between the user end and the mainframe. Instructions or data 1508 containing instructions to emit light 1502 may travel from mainframe 1504 to user end 1500. Data 1510 on received light 1512 may travel from user end 1500 to mainframe 1504. Mainframe 1504 may include a processor 1514 and also other components, such as light sources, detectors, display screen, source driver, controller, signal amplifier, and digitizer (see FIG. 2). Different means of transferring data are possible. In some embodiments, connection 1506a between mainframe 1504 and user end 1500 is comprised of a bundle of optical fibers that transfer light. In some other embodiments, the connection is comprised of electrical wires, preferably a ribbon cable because it is highly compact and flexible. In yet other embodiments, the connection is wireless and lacks a physical connection.

In some embodiments, a display screen 1518 displays diagnosis results, images, and other information 1516 the user may be interested in. Display screen 1518 may be part of mainframe 1504, exist remotely on another apparatus dedicated to the device, or be on the user's separate electronic device, such as a mobile phone or a personal computer. User end 1500 communicates with mainframe 1504 to exchange data and instructions 1508, 1510. Various embodiments have different combinations wherein components are placed in different places, as described below.

FIG. 15 is a schematic of a whole view of an embodiment, according to this invention, wherein connection 1506b between user end 1500 and mainframe 1504 is of electrical nature. Like parts are indicated by like reference numerals as used previously, so that repeated explanation is omitted here. The means of connection transfer only electrical signals. It delivers instructions 1508 from processor 1514 within mainframe 1504, enabling particular sources on user end 1500 to emit light 1502 at predetermined, particular wavelengths and/or predetermined, particular times as instructed. The detectors on user end 1500 register various reflected or diffracted light waves 1512. Data collected 1510 is transferred back to mainframe 1504, where useful data, such as sizes of areas of interest, depths of areas of interest, and images of the interior of the user's skin layers, are derived. Results derived 1516 can be displayed on screen 1518 for the user. Screen 1518 may be part of mainframe 1504, separate from mainframe 1504, or it could be on another device. For example, the screen may be on a mobile phone or a monitor of a personal computer may connect to mainframe 1504 and serve as the screen. Results 1516 may be sent to such a separate device, or it may be displayed on screen 1518 as part of mainframe 1504.

FIG. 16 is a schematic of a preferred embodiment, according to this invention, wherein like parts are indicated by like reference numerals as used previously, so that repeated explanation is omitted here. The main difference from FIG. 15 is that here, results 1516 are transferred to and displayed on a separate device or screen 1518, whereas all functions described in FIG. 15 are performed at the user end, i.e., user end 1500 contains the processor, sources, and detectors. Display screen 1518 is electrically connected to user end 1500.

FIG. 17 is a schematic diagram of a whole view of an embodiment, wherein the connection between user end 1500 and mainframe 1504 is of optical nature, able to transfer light. Like parts are indicated by like reference numerals as used previously, so that repeated explanation is omitted here. Here, instructions originate from user end 1500, and the sources operate to emit light 1502 at predetermined, particular wavelengths and/or predetermined, particular times. User end 1500 collects returning light waves 1512, which are directly transferred to mainframe 1504 via optical-fiber cable 1506*c*. Light received 1512 at the user end may be focused by a lens (not shown here) before being directly transferred through optical-fiber cable 1506*c*. Received optical signals 1512 are detected by detectors 1520, or a panel thereof, within mainframe 1504. Detected optical signals are processed to derive useful data 1516, such as confirming possible tumors, its size and location, and images of the interior of the user's skin layers. These data 1516 may be presented on display screen 1518. Screen 1518 may be part of mainframe 1504, separate from it, or it could be on another device. For example, the screen may be on a mobile phone or a monitor of a personal computer.

As a variation of this embodiment, in FIG. 18, optical-fiber cable 1506*c* transfers both emitted light 1502 and returning light 1512. Like parts are indicated by like reference numerals as used previously, so that repeated explanation is omitted here. The main difference from FIG. 17 is that in this embodiment, mainframe 1504 comprises both sources 1522 and detectors 1520. Using the unique properties of optical fibers, optical-fiber cable 1506*c* acts as a waveguide for light 1502, 1512 emitted from and returned to mainframe 1504, where the data is processed. In this embodiment, user end 1500 does not have any sources or detectors. It only acts as a mechanism to collect and focus light that is emitted and returned. As in the embodiment of FIG. 17, results 1516 may be sent to a separate device, or it may be displayed on screen 1518 as part of mainframe 1504.

FIG. 19 is a schematic of a preferred embodiment wherein the connection between user end 1500 and mainframe 1504 is wireless. Instructions 1508*c* to generate light 1502 and data 1510*c* on detected light 1512 are transmitted by wireless means. Instructions 1508*c* are generated from mainframe 1504, enabling particular sources on user end 1500 to emit light 1502 at predetermined, particular wavelengths and/or predetermined, particular times as instructed. The detectors on user end 1500 register various reflected or diffracted light waves 1512. Data 1510*c* collected is transferred wirelessly back to mainframe 1504, where useful data 1516, such as sizes of areas of interest, depths of areas of interest, and images of the interior of the user's skin layers, are derived. The results derived can be displayed on screen 1518 for the user. Screen 1518 may be part of mainframe 1504, separate from it, or it could be on another device. For example, the screen may be on a mobile phone or a monitor of a personal computer. [additional technical details on wireless functions?].

FIG. 20 is a schematic diagram of an embodiment in which all functions described in the previous FIG. 19 are performed at user end 1500, i.e., user end 1500 contains the processor, sources, and detectors. Like parts are indicated by like reference numerals as used previously, so that repeated explanation is omitted here. The main difference from FIG. 19 is that results 1516 are transferred, not from a separate mainframe but directly from user end 1500, to and displayed on a separate device or screen 1518. Display screen 1518 is connected to user end 1500 via wireless means.

Operational accuracy of the device can be improved by using a supplementary layer between the surface of the skin and the device. Refractive index n plays a role in characterizing biological tissues' response to optical illumination. The layer acts as an intermediary between two media of dissimilar refractive indices. For example, there is a disproportionate disparity between air and tissue if approximately n of air is 1.00, n of epidermis is 1.41, n of dermis is 1.36, and n of fatty tissue is 1.45. A medium with sufficiently disparate refractive index will tend to reflect light incident on that medium. The supplementary layer serves to introduce an intermediate n that mediates and bridges the gap between the disparate values between air and tissue, i.e., approximately between 1.00 and refractive indices of tissue components. Since the light incident must penetrate, the layer is transparent to light wavelengths of interest and reduces reflection. The layer is thin relative to the tissue, non-hazardous to the skin, and is easily removed or washed. The layer helps smooth out the target surface area of the skin, reducing variability and standardizing the experience among users of the device, because there may be different skin types, amount of hair present, and smoothness. Flattening the skin above the area the device operates on can reduce interference from microscopic obstacles and gaps present on the surface of the skin. The supplementary layer may be embodied and used in various ways as disclosed below.

Figure 21A:
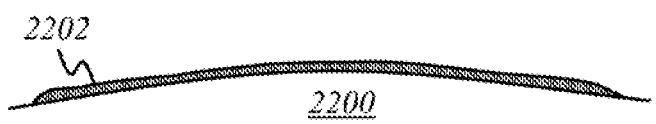
FIGS. 21A-21E show schematics of various forms of a supplementary layer used to improve functionalities of the present invention.
Figure 21B:
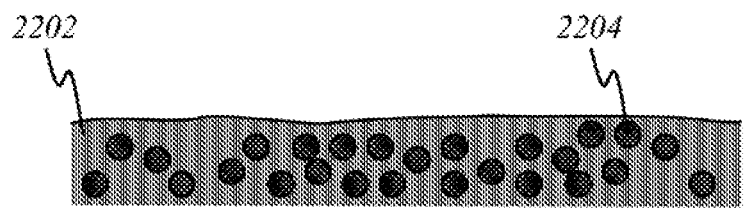

FIG. 21A illustrates a cross-sectional view of a section of skin 2200 and a gel layer 2202. A thin layer of gel 2202 is applied on the surface of section of skin 2200 over which the device will be placed. The thickness of the layer of gel 2202 is exaggerated to show the amorphous nature of gel 2202. It is easily washed from the skin as well as the device if the device has touched the gel. FIG. 21B is a highly enlarged cross-sectional view of the same section of skin 2200 as FIG. 21A. The main difference from FIG. 21A is that nanoparticles 2204 are embedded in gel 2202, which may be composed of ZnO, TiO2, and/or other metal oxide particles. Nanoparticles 2204 enable reduction or complete alleviation of the reflection of light, which enhances the clarity of images produced later.

Figure 21C:
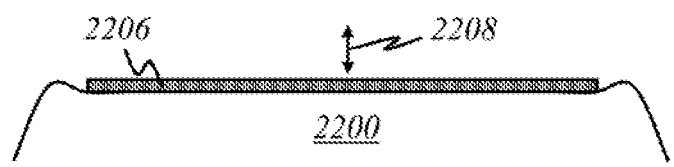

FIG. 21C illustrates a cross-sectional view of skin 2200 and a rigid layer 2206 pressing down on it. As with other forms of the supplementary layer, rigid layer 2206 is transparent to wavelengths of interest and is non-toxic to the skin.

By applying force 2208 during application of rigid layer 2206, it flattens skin 2200 and smoothes out the surface of skin 2200. This serves two purposes: Reduce the reflection of light and the delta of refractive indices between air and components of skin 2200, and reduce variability of experience among different users. Rigid layer 2206 may be constructed inexpensively to be disposable.

Figure 21D:
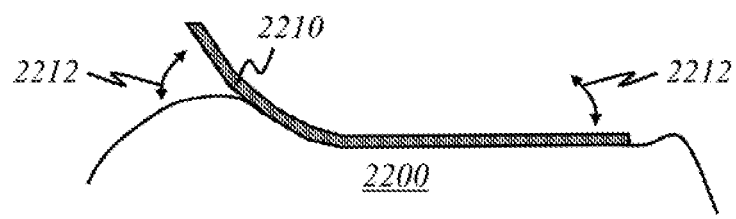
Figure 21E:
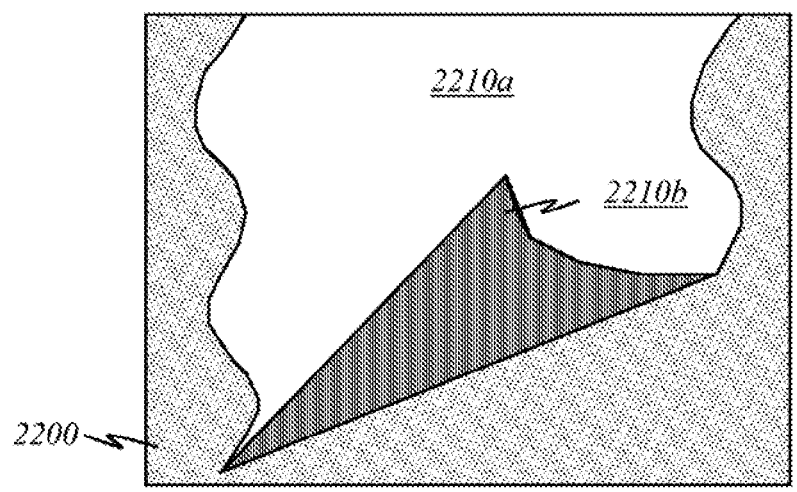

FIG. 21D illustrates a cross-sectional view of skin 2200 and one side of a flexible layer 2210 pressing down on it. As with other forms of the supplementary layer, flexible layer 2210 is transparent to wavelengths of interest and is non-toxic to the skin. Flexible layer 2210 may be extremely thin and malleable so as to be wrapped or stretched over the target area of skin. Similar to the rigid or gel embodiments as shown in FIGS. 21A-21C, flexible layer 2210 is serves to reduce the gap between disparate n values when light enters a different medium. By applying force 2212 toward or away during application of flexible layer 2210, the user has greater control over application of flexible layer 2210 as well as determination of which area of skin to apply it to. Flexible layer 2210 may be constructed inexpensively to be disposable. FIG. 21E is a schematic showing a top view of skin 2200 and a flexible layer 2210 as an alternative view of FIG. 21D. Top side 2210a of flexible layer 2210 is shown, and bottom side 2210b is shown being lifted from skin 2200. Flexible layer 2210 is malleable enough to be folded and partially bent upward as illustrated.

Figure 22A:
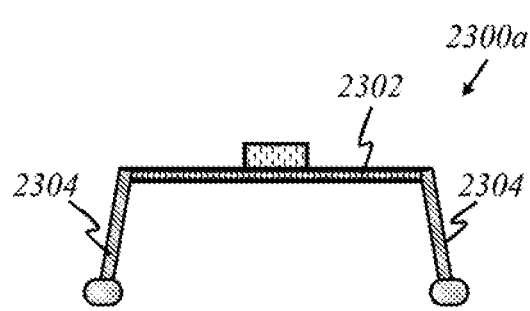

FIGS. 22A-22D are schematic diagrams of various examples of shapes of devices and manufactures in which the functions disclosed thus far may be implemented. FIG. 22A shows an example of an embodiment of a device that implements the present invention. A top view of a non-contact type device 2300a having center pane 2302 and side panes 2304 is shown. As described in the text accompanying FIGS. 11 and 12, each pane 2302, 2304 has sources or detectors, or both, or panels thereof. The capability to adjust pane angles introduces compactness and flexibility in operating the device depending on the size and location of the patch of skin having area of concern. This type of device may implement at least the non-contact embodiments shown in FIGS. 1 and 12.

Figure 22B:
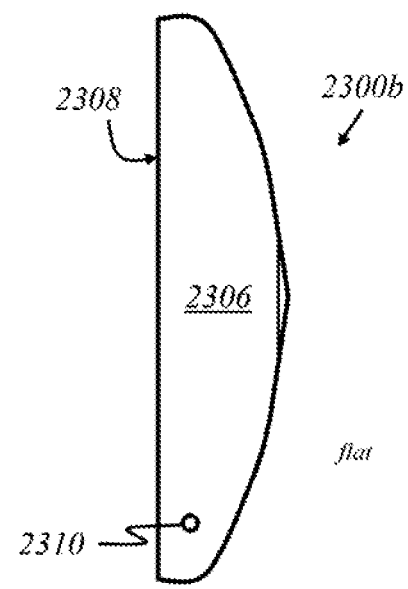

FIG. 22B shows another example of an embodiment of a device that implements the present invention and may implement at least the contact embodiments shown in FIGS. 8 and 9. A side view of a flat contact device 2300b having a user end 2306 is shown. An interfacing side 2308 of flat user end 2306 has a flat shape. Flat user end 2306 allows the user to press device 2300b to conform the skin to the shape of interfacing side 2308 of user end 2306. Direct contact enhances the quality of data acquired with a smaller margin of error. An example of a port 2310 is shown for connecting user end 2306 to other devices, such as a switch, control panel, display screen, computing device, and other peripheral devices, all of which may reside within user end 2306.

FIG. 22C shows another example of an embodiment of a device that implements the present invention and may implement at least the contact embodiments shown in FIGS. 6-8. An angled view is shown of a wearable-type device 2300c having a panel 2312 held around the user's appendage, such as finger or wrist, by using a rigid or flexible fastening apparatus 2314, such as a strap or metallic band. This allows device 2300c to be worn at all times for constant collection of data without manual operation. Panel 2312 may employ various ways to measure critical metabolites in the user's body. It may use a nano-membrane to collect bodily fluids as described in the text accompanying FIGS. 1A, 1C, 7A and 7B. It may use a rough surface with nanopores as described in the text accompanying FIGS. 7D-7F. It may use optical means, using light sources and light detectors as described in the text accompanying FIG. 7B. It may use an electronic circuit to measure resistivity in a channel of internal bodily fluids as described in the text accompanying FIGS. 8 and 9.

FIG. 22D shows another example of an embodiment of a device that implements the present invention and may implement at least the contact embodiments shown in FIGS. 10A and 10B. An angled view is shown of another wearable-type device 2300d amenable for use with eyeglasses. A panel 2316 of light sources and detectors is present on one or more sides of eyeglass device 2300d. This allows the device to worn at all times for constant collection of data through optical means without manual operation.

In the preferred embodiments, various ways are incorporated as a part of examples, but without limitation, for detecting the chemical matters inside body, their types, and their concentration.

The present invention is expected to be found practically useful for detecting the specific chemical matters such as blood sugars directly or indirectly. Furthermore, an apparatus is also described to transfer the data to the mobile device, or wirelessly sent to the electronic appliances. The apparatus can also be connected to the mobile device to achieve the image in the third device, outside of the apparatus, explained in the preferred embodiments.

Although, the invention has been described with respect to specific embodiment for complete and clear disclosure, the appended claims are not to be thus limited but are to be construed as embodying all modification and alternative constructions that may be occurred to one skilled in the art which fairly fall within the basic learning here is set forth.

The present invention is expected to be found practically use in the hand held based non-invasive screening system where the broadband and/or coherent radiation is used to screen and diagnosis fluids, their types, and their concentrations. The application includes not only hand held type screen/diagnosis system, but also combining with other system to increase the accuracy for the small to medium scale system.

Specific embodiments or examples, given in the detailed description of the present invention, are only used for clarifying the technical contents of the present invention, and are not narrowly interpreted in a limited manner to such specific examples, and various modifications may be made therein within the spirit of the present invention and the scope of the following claims.

What is claimed:

1. A sensing system for screening or diagnosis of diabetes comprising:
   an assembly comprising:
   a collection means, wherein the collection, means is configured to contact a skin of a subject for collecting a metabolite in a volume of biomass and passing through the collection means and wherein the collection means comprises of a plurality of pores and channels connected thereto;
   at least one wire, and;
   a device comprising:
   a first electrical contact;
   a second electrical contact;
   a first semiconductor of a first type;
   a second semiconductor of opposite type of the first type;
   wherein the first electrical contact is located on the first semiconductor;

wherein the second electrical contact is located on the second semiconductor;
a depletion layer located between the first semiconductor and the second semiconductor;
wherein an electrical signal flows through the first electrical contact and the second electrical contact based on a measured resistance due to the metabolite in the volume of biomass;
a storage device; and
a programmable device,
wherein the metabolite is selected from a group consisting of $CO_2$, $H^+$, and a combination thereof, and
wherein the programmable device derives a concentration of the metabolite in the volume of biomass based on the measured resistance caused by collection of a bodily fluids and a known correlation between the concentration of the metabolite and the measured resistance;
wherein the collection means passes the ions from the metabolite to the depletion layer;
wherein the first electrical contact and second electrical contact physically contact the collection means on sides opposite to one another;
wherein the first semiconductor second semiconductor and the depletion layer form a flat surface;
wherein a resistance value of the depletion layer varies on a concentration of ions that move though the collection means;
wherein the programmable device derives a concentration of the metabolite in the volume of biomass based on the measured resistance of the depletion layer;
wherein the collection means holds the volume of biomass on the surface of the device; and wherein the electrical signal represents the concentration of the metabolite in the volume of biomass.

2. The sensing system of claim 1, wherein the system further comprises an electric circuit, wherein a current flows through the circuit to generate a first resistance between a first point extended from the first electrical contact and a second point extended from the second electrical contact, wherein the programmable device can derive the concentration of the metabolite in the volume of biomass using the difference between the first resistance and a second resistance that is a known reference value.

3. The sensing system of claim 1, further comprises a display.

4. The sensing system of claim 1, wherein the programmable device is selected from a group consisting of a microprocessor, microcontroller, digital signal processor (DSP), field programmable gate array (FPGA), and a combination thereof.

5. The sensing system of claim 1, further comprising a fastening apparatus that forms an enclosure for an appendage.

6. The sensing system of claim 1, further comprising a fastening apparatus is wearable on a wrist or a finger.

7. The sensing system of claim 1, wherein the collection means further comprises a repeating pattern of micro- or nanoscale protrusions that cause the pores to collect the bodily fluids in a greater amount than would without the protrusions.

8. The sensing system of claim 1, wherein the collection means further comprises nanomembrane that separated ions such as $CO_2$, $H^+$, from larger molecules in the samples of bodily fluids.

9. The sensing system of claim 1, further comprises an interface in between the skin and the device.

10. The sensing system according to the claim 1, further comprising a socket located on the device.

11. The sensing system according to the claim 1, further comprising a cable to transfer a data.

* * * * *